United States Patent
Hamilton et al.

(10) Patent No.: US 6,911,023 B1
(45) Date of Patent: Jun. 28, 2005

(54) ABSORBENT ARTICLE WITH IMPROVED FASTENING SYSTEM

(75) Inventors: Raymond Scott Hamilton, Mason, OH (US); George Christopher Dobrin, Mason, OH (US); Mark James Kline, Cincinnati, OH (US); George Bartol Glackin, III, Wyoming, OH (US); Luke Robinson Magee, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/633,423

(22) Filed: Aug. 7, 2000

(51) Int. Cl.$^7$ .................................................. A61F 13/15
(52) U.S. Cl. ........................................ 604/387; 604/389
(58) Field of Search ................................ 604/386, 387, 604/391, 392, 389, 390; 24/442, 450, 306

(56) References Cited

U.S. PATENT DOCUMENTS

| | | |
|---|---|---|
| 3,848,594 A | 11/1974 | Buell |
| 3,860,003 A | 1/1975 | Buell |
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,381,781 A | 5/1983 | Sciaraffa et al. |
| 4,463,045 A | 7/1984 | Ahr et al. |
| 4,515,595 A | 5/1985 | Kievit et al. |
| 4,555,244 A | 11/1985 | Buell |
| 4,573,986 A | 3/1986 | Minetola et al. |
| 4,609,518 A | 9/1986 | Curro et al. |

(Continued)

FOREIGN PATENT DOCUMENTS

| | | |
|---|---|---|
| CA | 2257440 A1 | 9/1999 |
| EP | 0 847 738 A1 | 6/1998 |
| WO | WO 93/25172 A1 | 12/1993 |
| WO | WO 94/14395 A1 | 7/1994 |
| WO | WO 95/13775 A1 | 5/1995 |
| WO | WO 95/16746 A1 | 6/1995 |
| WO | WO 95/24173 A3 | 9/1995 |
| WO | WO 98/03328 A1 | 1/1998 |
| WO | WO 98/47781 A1 | 10/1998 |

*Primary Examiner*—John J. Calvert
*Assistant Examiner*—Michele Kidwell
(74) *Attorney, Agent, or Firm*—Jack L. Oney, Jr.; Jay A. Krebs; Ken K. Patel

(57) ABSTRACT

An article to be worn about a wearer including an fastening system joined to the article including a receiving member having at least a first receiving fastening element and a second receiving fastening element. The first receiving fastening element is disposed on a flap having a proximal portion joined to the article and a distal portion extending from the proximal portion. The second receiving fastening element is disposed so as to be generally in face to face relationship with the first receiving fastening element when the receiving member is in a closed configuration. An engaging member includes at least a first engaging fastening element and a second engaging fastening element. The first engaging fastening element is engageable with at least the first receiving fastening element and the second engaging fastening element is engageable with at least the second receiving fastening element. The fastening system may be unbalanced; the second flap may be substantially unjoined to the article; the receiving member may have a hinge oriented substantially parallel to a primary direction of load bearing; and/or the fastening system may have a peel resistance in a direction other than the primary direction of load bearing greater than or equal to about 1000 grams.

37 Claims, 14 Drawing Sheets

U.S. PATENT DOCUMENTS

| | | | |
|---|---|---|---|
| 4,610,678 A | 9/1986 | Weisman et al. | |
| 4,629,643 A | 12/1986 | Curro et al. | |
| 4,662,874 A | 5/1987 | Korpman | |
| 4,673,402 A | 6/1987 | Weisman et al. | |
| 4,695,278 A | 9/1987 | Lawson | |
| 4,699,622 A | 10/1987 | Toussant et al. | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |
| 4,816,025 A | 3/1989 | Foreman | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,888,231 A | 12/1989 | Angstadt | |
| 4,894,060 A * | 1/1990 | Nestegard | 604/391 |
| 4,909,803 A | 3/1990 | Aziz et al. | |
| 4,938,753 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,988,344 A | 1/1991 | Reising et al. | |
| 4,988,345 A | 1/1991 | Reising | |
| 4,990,147 A | 2/1991 | Freeland | |
| 4,991,234 A | 2/1991 | Greenberg | |
| 5,006,394 A | 4/1991 | Baird | |
| 5,026,364 A | 6/1991 | Robertson | |
| 5,076,288 A | 12/1991 | Millard et al. | |
| 5,137,537 A | 8/1992 | Herron et al. | |
| 5,142,743 A * | 9/1992 | Hahn | 24/16 R |
| 5,147,345 A | 9/1992 | Young et al. | |
| 5,151,092 A | 9/1992 | Buell et al. | 604/385.2 |
| 5,171,236 A | 12/1992 | Dreier et al. | |
| 5,221,274 A | 6/1993 | Buell et al. | |
| 5,242,436 A | 9/1993 | Weil et al. | |
| 5,260,345 A | 11/1993 | DesMarais et al. | |
| 5,267,992 A | 12/1993 | Van Tilburg | |
| 5,269,755 A | 12/1993 | Bodicky | |
| 5,269,776 A | 12/1993 | Lancaster et al. | |
| 5,306,266 A | 4/1994 | Freeland | |
| 5,318,555 A | 6/1994 | Siebers et al. | |
| 5,324,279 A | 6/1994 | Lancaster et al. | |
| 5,342,338 A | 8/1994 | Roe | |
| 5,342,344 A | 8/1994 | Lancaster et al. | |
| 5,374,262 A | 12/1994 | Keuhn, Jr. et al. | |
| 5,387,207 A | 2/1995 | Dyer et al. | |
| 5,389,094 A | 2/1995 | Lavash et al. | |
| 5,397,318 A | 3/1995 | Dreier | |
| 5,399,219 A * | 3/1995 | Roessler et al. | 156/259 |
| 5,499,978 A | 3/1996 | Buell et al. | |
| 5,507,736 A | 4/1996 | Clear et al. | |
| 5,514,121 A | 5/1996 | Roe et al. | |
| 5,518,801 A | 5/1996 | Chappell et al. | |
| 5,540,671 A | 7/1996 | Dreier | |
| 5,545,159 A | 8/1996 | Lancaster et al. | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,595,567 A | 1/1997 | King et al. | |
| 5,607,760 A | 3/1997 | Roe | |
| 5,609,587 A | 3/1997 | Roe | |
| 5,624,427 A | 4/1997 | Bergman et al. | |
| 5,624,428 A * | 4/1997 | Sauer | 604/391 |
| 5,625,222 A | 4/1997 | Yoneda et al. | |
| 5,635,191 A | 6/1997 | Roe et al. | |
| H1670 H | 7/1997 | Aziz et al. | |
| 5,643,588 A | 7/1997 | Roe et al. | |
| 5,653,703 A | 8/1997 | Roe et al. | |
| 5,669,897 A | 9/1997 | Lavon et al. | |
| 5,713,111 A | 2/1998 | Hattori et al. | |
| 5,735,840 A | 4/1998 | Kline et al. | |
| 5,741,318 A | 4/1998 | Ouellette et al. | |
| 5,845,375 A | 12/1998 | Miller et al. | |
| 5,846,365 A | 12/1998 | Kline et al. | |
| 5,860,945 A | 1/1999 | Cramer et al. | |
| 5,865,823 A | 2/1999 | Curro | |
| 5,897,545 A | 4/1999 | Kline et al. | 604/386 |
| 5,926,926 A * | 7/1999 | Kato | 24/442 |
| 5,938,648 A | 8/1999 | LaVon et al. | |
| 5,941,864 A | 8/1999 | Roe | |
| 5,968,025 A | 10/1999 | Roe et al. | |
| 5,971,970 A | 10/1999 | Carlbark et al. | |
| 5,977,430 A | 11/1999 | Roe et al. | |
| 5,984,911 A | 11/1999 | Siebers et al. | 604/391 |
| 5,987,545 A | 11/1999 | Oh | |
| 5,997,520 A | 12/1999 | Ahr et al. | |
| 5,997,521 A | 12/1999 | Robles et al. | |
| 6,004,306 A | 12/1999 | Robles et al. | |
| 6,007,527 A * | 12/1999 | Kawaguchi et al. | 604/386 |
| 6,013,063 A | 1/2000 | Roe et al. | |
| 6,102,901 A | 8/2000 | Lord et al. | 604/386 |
| 6,251,097 B1 * | 6/2001 | Kline et al. | 604/387 |
| 6,432,098 B1 | 8/2002 | Kline et al. | |
| 6,572,601 B2 * | 6/2003 | Suprise et al. | 604/391 |
| 2002/0016581 A1 * | 2/2002 | Kline et al. | 604/386 |
| 2002/0095131 A1 * | 7/2002 | Olson | 604/391 |
| 2002/0173768 A1 * | 11/2002 | Eisberg et al. | 604/391 |

* cited by examiner

ABSORBENT ARTICLE WITH IMPROVED FASTENING SYSTEM

FIELD OF THE INVENTION

The present invention relates to absorbent articles such as diapers, training pants, bibs, sanitary napkins and the like. More specifically, the present invention relates to absorbent articles including improved fastening systems.

BACKGROUND OF THE INVENTION

Absorbent articles and disposable absorbent articles such as diapers, training pants, bibs, sanitary napkins and the like are well known in the art. Such articles are typically used to absorb and contain bodily exudates such as feces, urine and/or menses. Until fairly recently, many of the absorbent articles identified above were made from reusable materials such as woven cloth materials including cotton and other absorbent fabrics. Lately, however, many consumers have found that using disposable absorbent articles is more convenient than using reusable articles for various reasons. Accordingly, many different types of disposable absorbent articles, including disposable diapers such as those described in U.S. Pat. No. 5,151,092 entitled "Absorbent Article With Dynamic Elastic Waist Feature Having Predisposed Flexural Hinge" issued to Buell et al. on Sep. 22, 1992 have achieved wide acceptance and commercial success.

Over the years, there have been many advancements related to disposable absorbent articles, including improvements in fastening systems, absorbency and aesthetics. However, there is still a need for improvement relating to fit, comfort, aesthetics and overall performance of such articles. For example, disposable diapers often do not look or feel like garments. Further, disposable diapers are often difficult for the user, whether it be the caregiver or child, to properly fasten about the wearer. This can lead to poor fit which can result in leaks and/or reduced comfort for the wearer. Further, in refastenable pull-on diapers, such as described in U.S. Pat. No. 5,987,545 issued to Kline et al., multi-directional resistance to disengagement is important to ensure that the fasteners remain engaged while pulling up the product so that the product does not come apart during application.

One example of an attempt to improve on fastening systems for absorbent articles is disclosed in U.S. Pat. No. 5,984,911 issued to Siebers et al. The patent discloses a fastening system including a foldable trapping panel with a base stationary on the front of the article and a flap panel which extends out from the base. Both the base and the flap include the loop components of a hook and loop fastening device. A complementary hook fastening element is attached to the back of the diaper. Although this system is disclosed to provide improved performance for hook and loop type fastening system, it may not provide the specific performance necessary to function as needed for all product designs, such as for a refastenable pull-on diaper. Further, a fundamental understanding of how such a system works is not disclosed, nor are embodiments that take full advantage of the system.

Accordingly, it would be desirable to provide an absorbent article with an improved fastening system. It would also be desirable to provide an absorbent article with improved aesthetics. It would also be desirable to provide an absorbent article with improved fit and overall performance. Further, it would be desirable to provide an absorbent article with an improved fastening system that provides improved aesthetics and preferable easier and more reliable fastening performance.

SUMMARY OF THE INVENTION

An article to be worn about a wearer including an fastening system joined to the article including a receiving member having at least a first receiving fastening element and a second receiving fastening element. The first receiving fastening element is disposed on a flap having a proximal portion joined to the article and a distal portion extending from the proximal portion. The second receiving fastening element is disposed so as to be generally in face to face relationship with the first receiving fastening element when the receiving member is in a closed configuration. An engaging member includes at least a first engaging fastening element and a second engaging fastening element. The first engaging fastening element is engageable with at least the first receiving fastening element and the second engaging fastening element is engageable with at least the second receiving fastening element. The fastening system may be unbalanced; the second flap may be substantially unjoined to the article; the receiving member may have a hinge oriented substantially parallel to a primary direction of load bearing; and/or the fastening system may have a peel resistance in a direction other than the primary direction of load bearing greater than or equal to about 1000 grams.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

As used herein, the term "absorbent article" refers to devices which absorb and contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
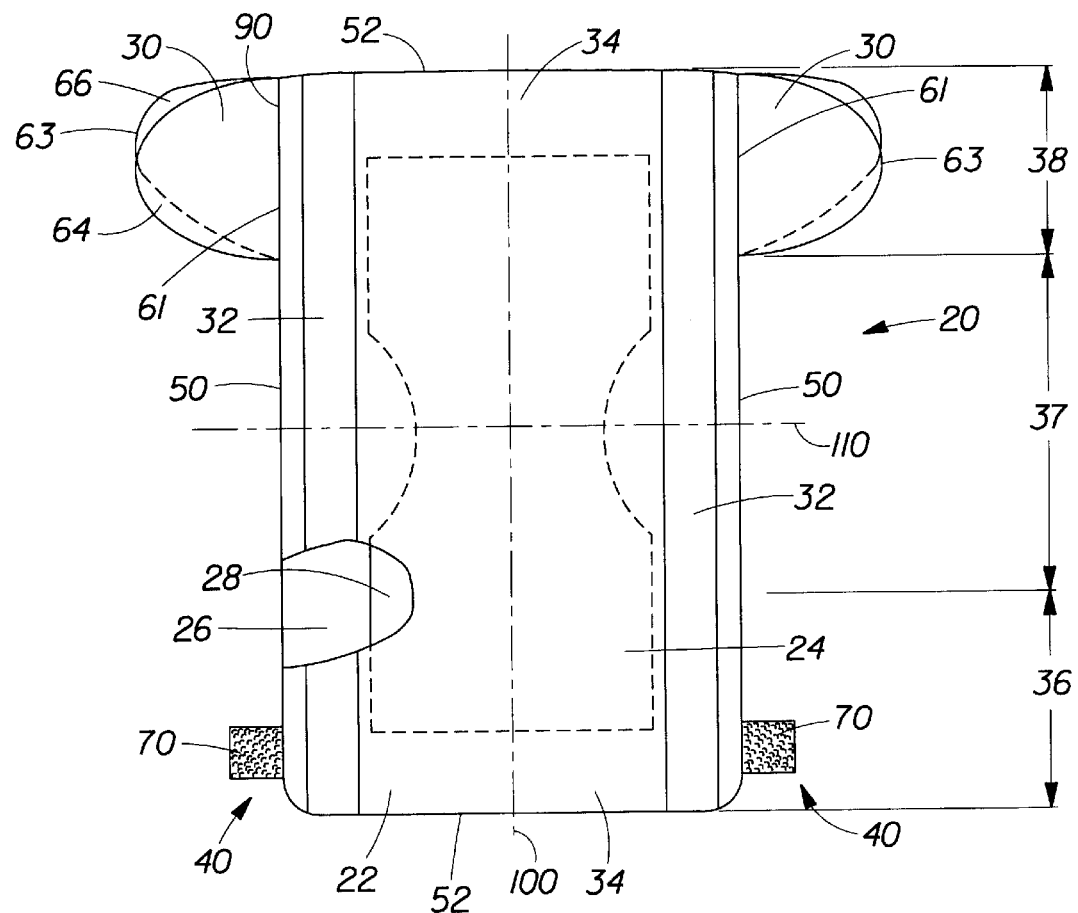
FIG. 1 is a plan view of one embodiment of the present invention in a flat-out, state with portions of the structure being cut-away to more clearly show the construction the article.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28 which is preferably positioned between at least a portion of the topsheet 24 and the backsheet 26; side panels 30; elasticized leg cuffs 32; a waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering including the topsheet 24 and/or the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The backsheet 26 is generally that portion of the diaper 20 positioned adjacent garment facing surface of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent body surface of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 30 may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 24 can be found in U.S. Statutory Invention Registration No. H1670 published on Jul. 1, 1997 in the names of Aziz et al. Each of these references is hereby incorporated by reference herein. Alternatively, the topsheet 24 may include an apertured web or film which is hydrophobic. This may be accomplished by eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; and U.S. Pat. No. 5,968,025 entitled "Absorbent Article Having a Lotioned Topsheet" issued to Roe et al. on Oct. 19, 1999. The lotion may function alone or in combination with another agent as the hydrophobizing treatment described above. The topsheet 24 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. (As used herein, the term "disposed" is used to mean that an element (s) of the diaper is formed Joined and positioned) in a particular place or position as a unitary structure with other elements of the diaper or as a separate element joined to another element of the diaper.) The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in European Patent Application No. EP 0 847 738 A1 entitled "Disposable Absorbent Article Having Capacity to Store Low-Viscosity Fecal Material" published Jun. 17, 1998 in the name of Roe and U.S. Pat. No. 5,941,864 entitled "Disposable Absorbent Article Having Improved Fecal Storage" issued to Roe on Aug. 24, 199, both of which are hereby incorporated by reference herein. Further, the sublayer, or any portion thereof, may include or be coated with a lotion or other known substances to add, enhance or change the performance or other characteristics of the element.

The diaper 20 may also comprise at least one waist feature 34 that helps to provide improved fit and containment. The waist feature 34 may be elastic and/or extensible, or neither elastic or extensible. If the waist feature 34 is elastic or extensible, it will generally be designed to dynamically fit the wearer's waist. The waist feature 34 preferably extends at least longitudinally outwardly from at least one waist edge of the absorbent core 28 and generally forms at least a portion of the end edge 52 of the diaper 20. Disposable diapers are often constructed so as to have two waist features, one positioned in the first waist region 36 and one positioned in the second waist region 38. Further, while the waist feature 34 or any of its constituent elements may comprise one or more separate elements affixed to the diaper 20, the waist feature 34 may be constructed as an extension of other elements of the diaper 20, such as the backsheet 26, the topsheet 24, or both the backsheet 26 and the topsheet 24.

The waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; and U.S. Pat. No. 6,004,306 entitled "Absorbent Article With Multi-Directional Extensible Side Panels" issued to Robles et al. on Dec. 21, 1999; each of which is incorporated herein by reference.

The diaper 20 preferably further includes leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs 32 with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; PCT Application WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,62,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and 6,013,063 issued to Roe et al. on Jan. 11, 2000. All of the above-cited references are hereby incorporated by reference herein.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. Another exemplary fastening system is disclosed in co-pending U.S. application Ser. No. 09/143,184 entitled "Absorbent Article Fastening Device" in the names of Kline et al. filed on Aug. 8, 1998. The fastening system 40 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997. Each of these patents and the co-pending application are incorporated herein by reference. In alternative embodiments, opposing sides of the article may be seamed or welded to form a pant. This allows the article to be used as a pull-on type diaper, such as a training pant.

Figure 2:
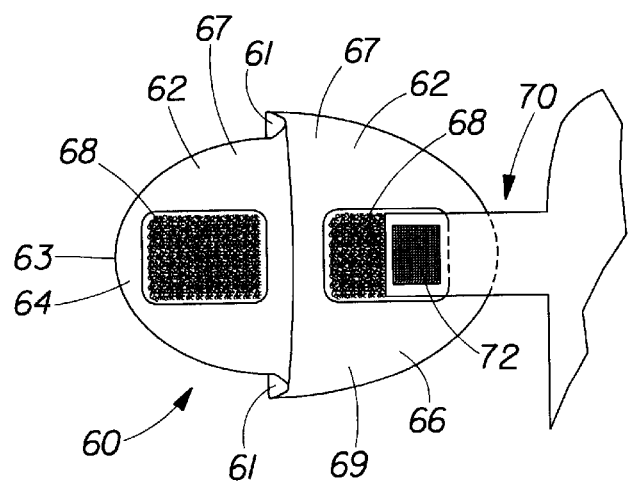
FIG. 2 is a partial plan view of a portion of one embodiment of a fastening system of the present invention.

In one preferred embodiment of the present invention, the fastening system 40 includes a receiving member and an engaging member. As shown in FIG. 2, the receiving member 60 may be disposed in at least a portion of the second waist region and may include two or more flaps 62, such as first flap 64 and second flap 66. Each of the flaps has an inner surface 67, an outer surface 69, a proximal portion 61 and a distal portion 63. The proximal portion 61 of the flap 62 is that portion of the flap 62 which is joined to the article 20, either directly or indirectly. The distal portion 63 of the flap 62 is the portion which extends from the proximal portion 61 and is generally not permanently joined to the underlying structure of the article 20. For example, as shown in FIG. 1, the proximal portion 61 of the flap 62 may be joined to the article and the distal portion 63 of the flap 62 may be unjoined to the underlying structure of the chassis 22 and may extend laterally outwardly from the proximal portion 61. It should be noted however, that embodiments are contemplated and further disclosed wherein the distal portion 63 may extend longitudinally outwardly, laterally inwardly and/or longitudinally inwardly from the proximal portion 61, depending on the orientation of the receiving member 60 on the article 20.

Figure 6:
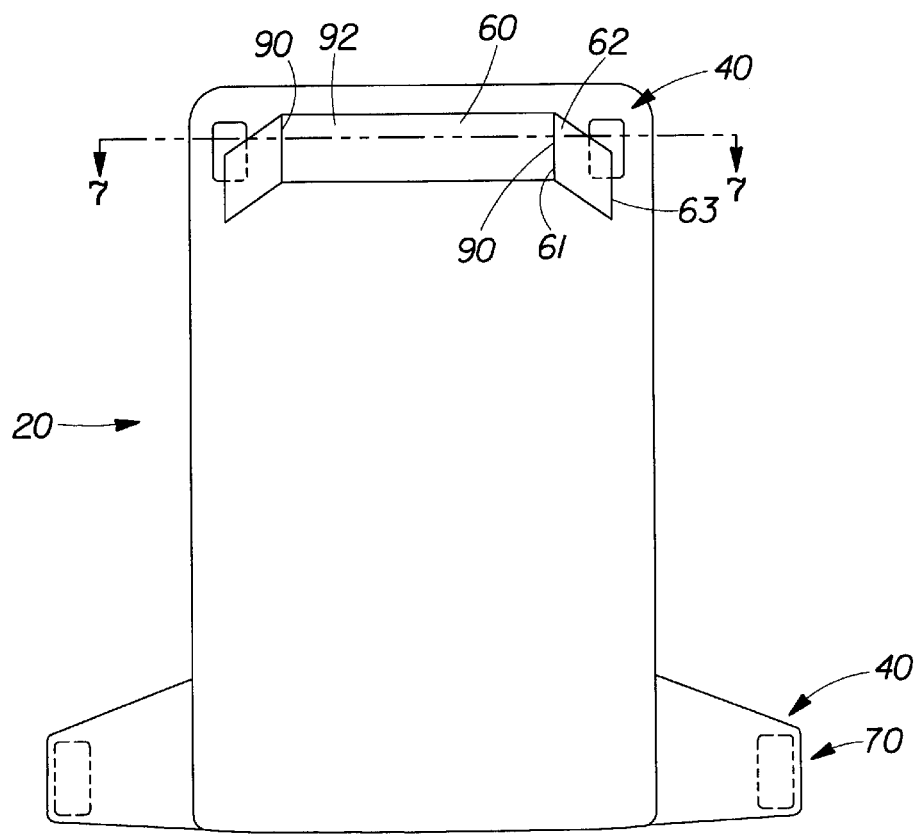
FIG. 6 is a plan view of an absorbent article including one embodiment of the fastening system of the present invention.
Figure 23:
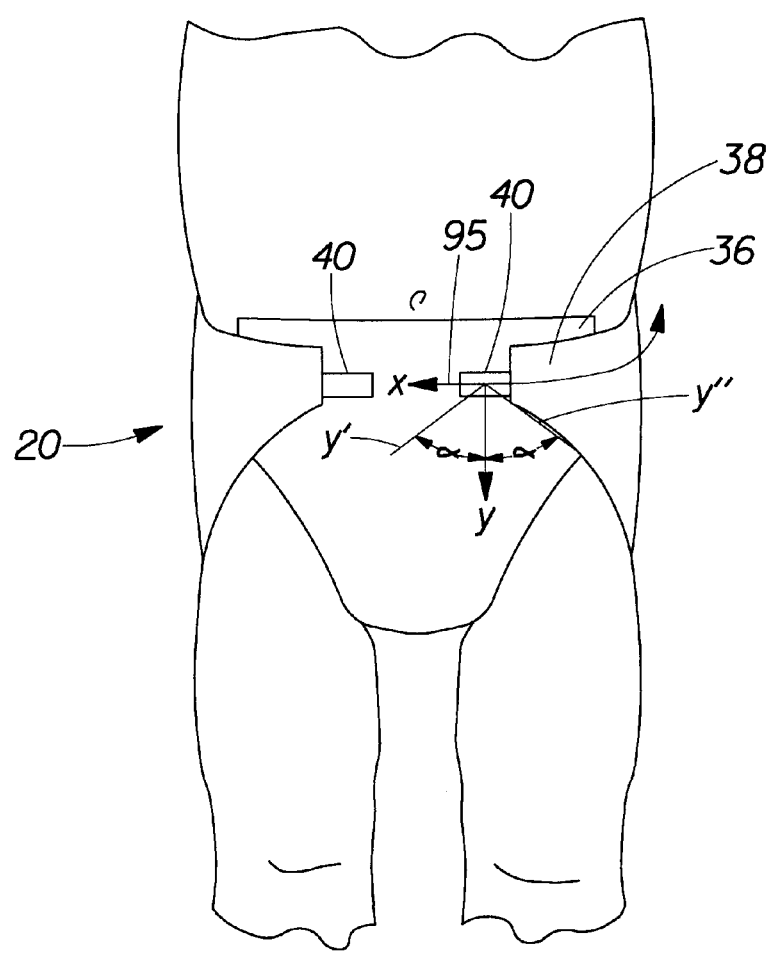
FIG. 23 is a perspective view of one embodiment of the present invention fastened about a wearer.

In some preferred embodiments of the present invention the receiving member 60 of the fastening system 40 may also include one or more hinges 90. The hinge 90 may be located at the connection of one or more of the flaps 62 to the diaper 20, or at the connection of one flap to another flap. As shown in FIG. 1, the hinge 90 may be located between the first flap 64 and the second flap 66. In an alternative embodiment, as shown in FIG. 6, the hinge 90 may be disposed adjacent the location where the flap 62 is joined to or extends from the article 20. In any case, the hinge 90 may be oriented generally in the primary plane of the load bearing and in a direction generally perpendicular to, generally parallel to or at an angle between generally perpendicular to and parallel to the primary direction of load bearing 95. The primary direction of load bearing 95 of a diaper in a fastened configuration on a wearer is generally directed around the waist circumference formed by the first and second waist regions in a fastened configuration such as shown in FIG. 23. The primary plane of load bearing of a diaper in a fastened configuration on a wearer is generally directed to the plane formed by the surface of the product generally parallel to the surface of the wearer's body at any given point when fastened in a configuration for wearing.

Configuring the hinge 90 in a direction angled or otherwise non-perpendicular relative to the primary direction of load bearing may provide several advantages. For example, the hinge 90 may be oriented to further isolate the flap fastening elements 68 from multi-directional peel forces, such as forces directed at the bottom edge of the flap fastening elements 68, or the top edge of the flap fastening elements 68. Such configurations may be especially advantageous for pull-on application of a diaper. This is because the act of pulling the diaper into position on the wearer may provide the diaper's fastening system with peel forces from multiple different directions. For example, the user may grasp the side panels 30 from the lower edge to pull the product up. Orienting the hinge 90 parallel to the primary direction of load bearing and locating it near the lower edge of the flap fastening elements 68 may isolate the flap fastening elements 68 from forces that might otherwise cause the flap fastening elements 68 to disengage in such a scenario. Further, as described in more detail below, configuring the hinge 90 in a direction angled relative to the primary direction of load bearing can improve fit and reduce the risk of skin marking. Thus, locating the hinge 90 in a particular direction on the article may allow for greater peel resistance for particular product configurations as well as improved fit and/or reduced skin marking.

In certain embodiments, the receiving member 60 may include multiple flaps 64 and 66 each having distinct hinges 91 and 93. The hinges 91 and 93 may vary in location and/or orientation relative to the primary direction of load bearing. For example, at least one hinge 91 of one flap 64 of the receiving member 60 may be oriented in a different direction relative to the primary direction of load bearing relative to the hinge 93 of at least one other flap 66. Alternatively, at least one flap 64 may include a hinge 91 in one location and/or orientation relative to the primary direction of load bearing and at least one other flap 66 may include a hinge 93 that is laterally and/or longitudinally offset from the hinge 91 of at least one other flap 64 and/or may be oriented differently relative to the primary direction of load bearing than the hinge 91 of the at least one other flap 64.

Figure 24:
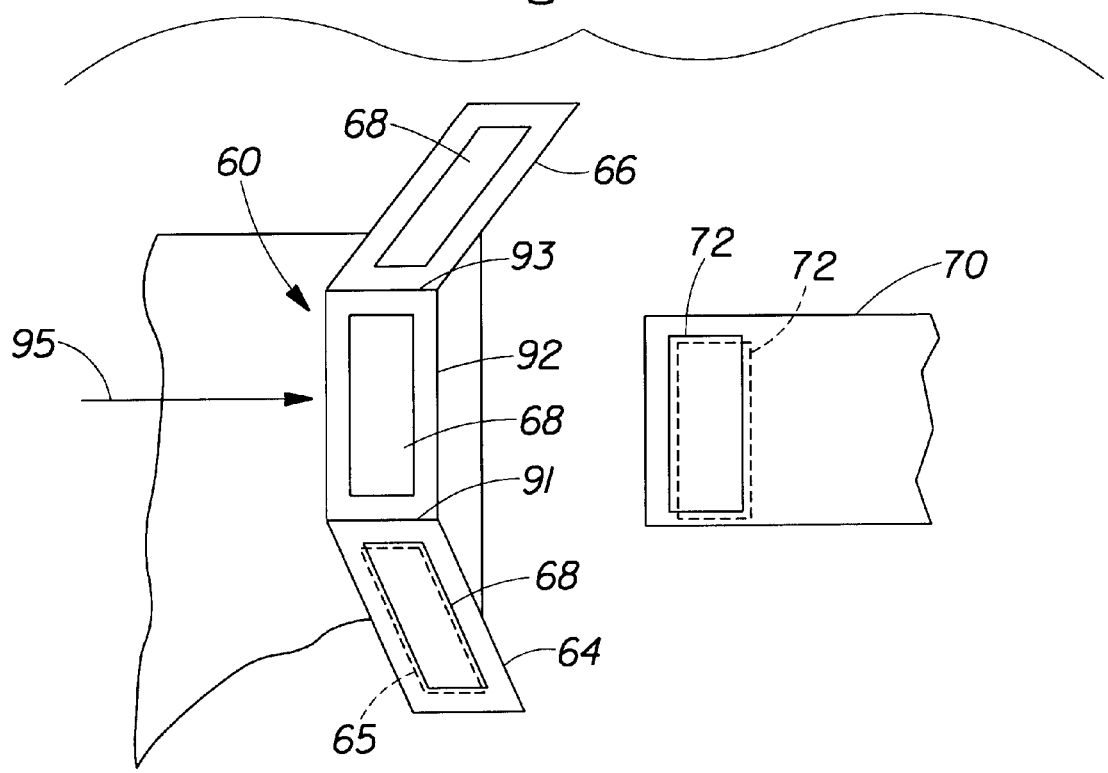
FIG. 24 is a perspective view of one embodiment of a fastening system of the present invention in an unfastened configuration.
Figure 25:
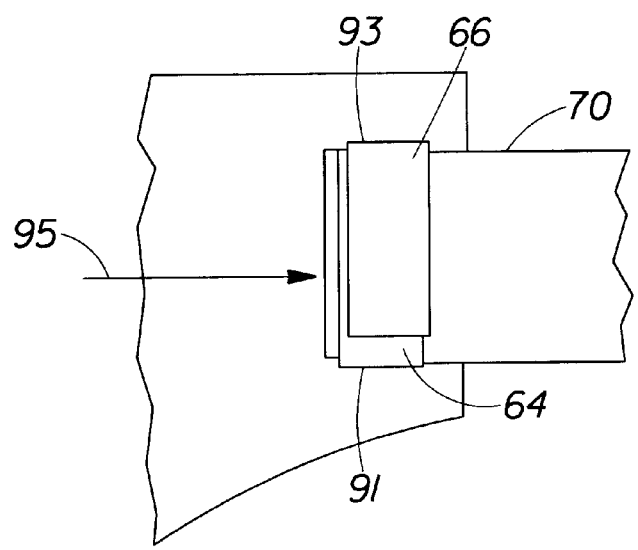
FIG. 25 is a perspective view of the fastening system shown in FIG. 24 in a fastened configuration.

In the embodiment shown in FIGS. 24 and 25, for example, the receiving member 60 includes two flaps 64 and 66 and base 92. Base 92 is at least partially joined to the underlying structure of the article. Alternatively, base 92 may be replaced with a portion of the backsheet or another structure of article 20 or may be a separate element joined to the article 20. Flaps 64 and 66 extend outwardly from the base 92 at hinges 91 and 93, respectively. In this embodiment, the hinges 91 and 93 are oriented parallel to the primary direction of load bearing 95 and are longitudinally offset from each other. At least one of the flaps 64 and 66 at least partially overlap the engaging member 70 in a fastened configuration as shown in FIG. 25. Preferably, the flaps 64 and 66 at least partially overlap each other in a fastened configuration. Each of the flaps 64 and 66 include at least one fastening element 68 that may engage with a fastening element 72 of the engaging member 70 or with a supplemental fastening element 65 of another flap. Any suitable fasteners may be used as the supplemental fastening element 65 such as hooks, loops, snaps, adhesive, cohesive, magnets, hermaphroditic fasteners, tab and slot fasteners, interlocking projections and receptacles fasteners, buckles or any combination of any of these or other fasteners. Examples of hermaphroditic fasteners, for example, are described in U.S. Pat. No. 5,845,375 issued to Miller et al. on Dec. 8, 1998 and in U.S. Pat. No. 5,713,111 issued to Hattori et al. on Feb. 3, 1998. Examples of interlocking projections and receptacles fasteners are described in U.S. Pat. No. 5,324,279 issued to Lancaster et al. on Jun. 28, 1994, U.S. Pat. No. 5,269,776 issued to Lancaster et al. on Dec. 14, 1993, U.S. Pat. No. 5,545,159 issued to Lancaster et al. on Aug. 13, 1996, U.S. Pat. No. 5,342,344 issued to Lancaster et al. on Aug. 30, 1994, and published patent applications WO 98/47781 published Oct. 29, 1998 by May and WO 98/03328 published Jan. 29, 1998 by Johnson. Hinges 91 and 93 in this embodiment prevent the engaging member 70 from disengaging with the receiving member 60 in a peel mode due to a force oriented primarily in a direction perpendicular to the primary direction of load bearing 95.

Figure 26:
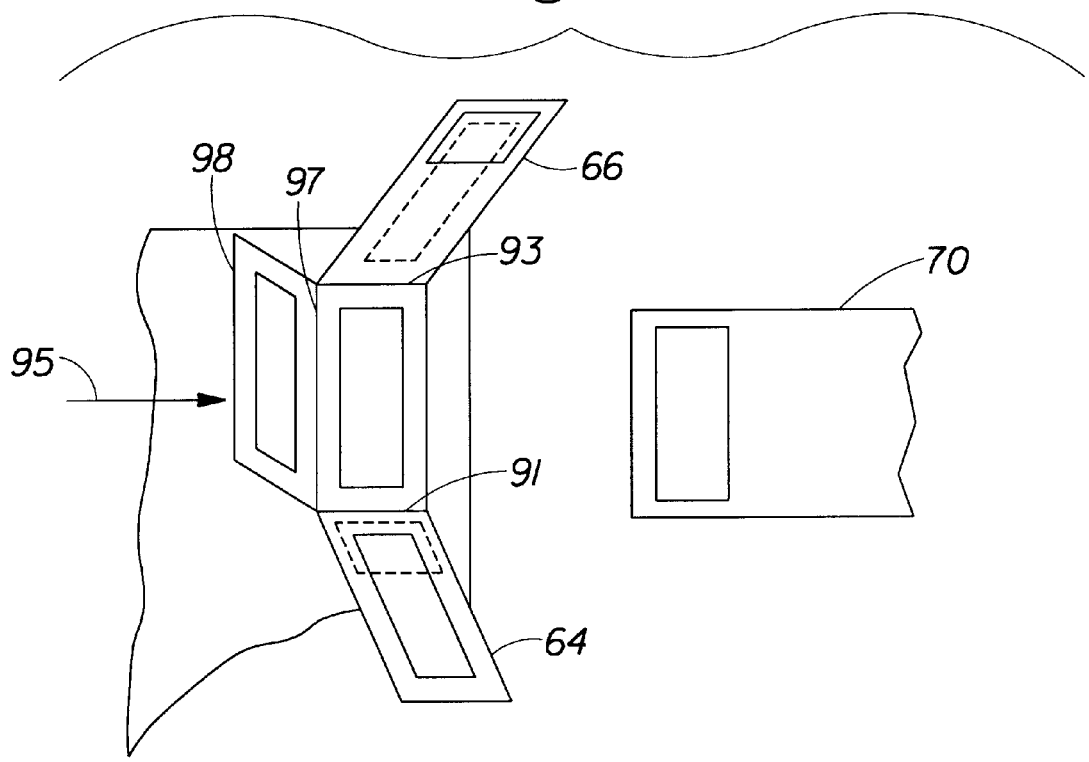
FIG. 26 is a perspective view of one embodiment of a fastening system of the present invention in an unfastened configuration.
Figure 27:
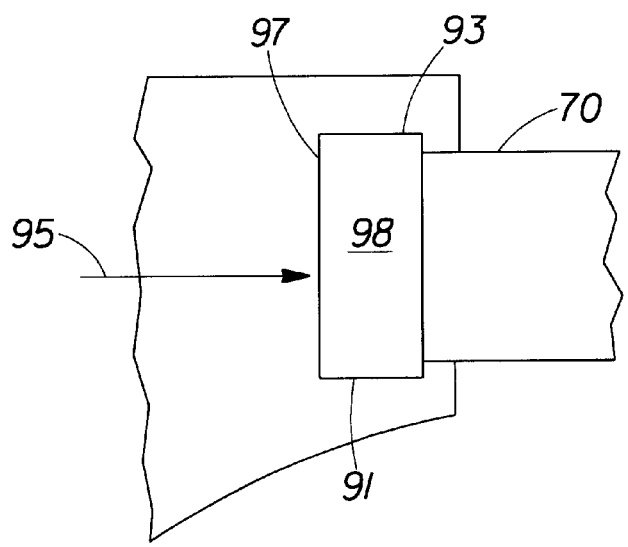
FIG. 27 is a perspective view of the fastening system shown in FIG. 26 in a fastened configuration.

Alternatively, the receiving member 60 may include hinges oriented in varied directions relative to the primary direction of load bearing 95 such as shown in FIGS. 26 and 27. In this embodiment, the receiving member 60 includes flaps 64 and 66 and base 92 similar to those shown and described with respect to FIGS. 24 and 25. The receiving member 60 further includes a third flap 98 having a third hinge 97. Hinge 97 is oriented perpendicular to the primary direction of load bearing 95 and serves to prevent the engaging member from disengaging at hinge 97 with the receiving member 60 in a peel mode due to a force oriented primarily in a direction parallel to the primary direction of load bearing 95. Alternatively, the receiving member 60 may include fewer or more flaps. For example, the receiving member 60 may include flaps 64 and 98 without flap 66 or may include flaps 66 and 98 without flap 64.

The first and second flaps 64 and 66 of the receiving member 60 may be the same or different in size, shape, material and/or construction. Further, either or both the first flap 64 and second flap 66 may be separate pieces of material joined to the chassis 22 or may comprise a portion of a different part of the article, such as the topsheet, backsheet, cuff material, waist member, etc. In any case, all or a portion of either or both first and second flaps 64 and 66 may be extensible, non-extensible or elastomeric. For example, a vacuum formed elastomer material such as described in U.S. patent application Ser. No. 08/816,106 filed on Mar. 14, 1997, which is incorporated by reference, may be used. Any other extensible and/or elastomeric/elastic materials, including those previously referenced herein, may also be used. Further, one or both of the flaps 62 may be at least partially breathable and/or water vapor permeable, liquid pervious or impervious.

Figure 3:
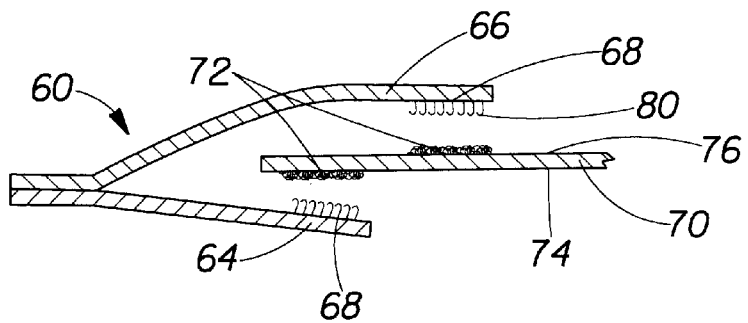
FIG. 3 is a partial cross-sectional view of one embodiment of the fastening system of the present invention.
Figure 4:
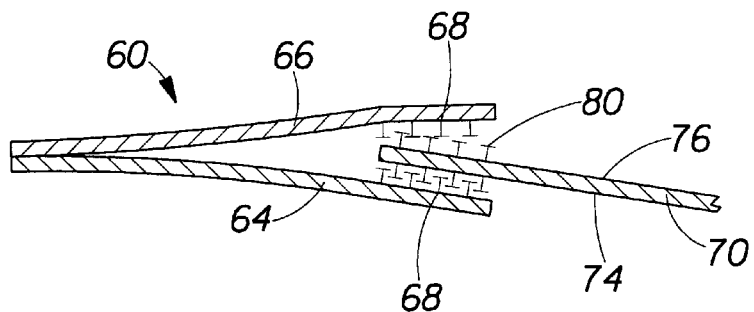
FIG. 4 is a partial cross-sectional view of one embodiment of the fastening system of the present invention.
Figure 5:
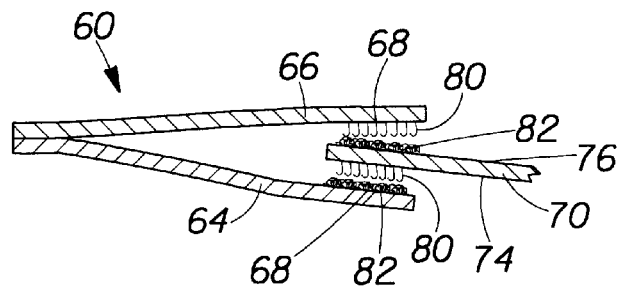
FIG. 5 is a partial cross-sectional view of one embodiment of the fastening system of the present invention.

The flaps 62 of the receiving member 60 may include one or more flap fastening elements 68, preferably disposed on at least a portion of the inner surface of the flap 62. The flap fastening elements 68 may comprise any known fastening means, such as hooks, loops, snaps, adhesive, cohesive, magnets, hermaphroditic fasteners, tab and slot fasteners, buckles or any combination of any of these or other fasteners. Further, the flap fastening elements 68 may be discrete pieces of material added to the flaps 62 or may be integrally formed from the material making up all or a portion of the flaps 62. As shown in FIG. 2, the flap fastening elements 68 may be substantially similar in size, shape and material to each other and may be disposed on the inner surface of each of the flaps 62. Alternatively, the flap fastening elements 68 may be different from each other in type, shape, size, location and/or fastening characteristics. One example of an alternative embodiment is shown in FIG. 5 wherein the receiving member 60 includes a first flap 64 comprising a loop-type 82 flap fastening element 68 and a second flap 66 comprising a hook-type 80 flap fastening element 68. Another example is shown in FIG. 3 wherein the location of the flap fastening element 68 disposed on the first flap 64 is at least partially offset from the flap fastening element 68 disposed on the second flap 66. Although FIG. 3 shows the location of the flap fastening element 68 offset in the lateral direction (i.e. parallel to the lateral centerline 110 of the article 20), the location of the fastening elements 68 can be varied in either or both the longitudinal or lateral directions, as desired.

As shown in FIGS. 1 and 2, the fastening system of the present invention preferably also includes at least one engaging member 70. The engaging member 70 may be configured to engage with the receiving member 60 to fasten the article 20 about the wearer or in a configuration for disposal. In any case, the engaging member may be any suitable element joined to or integral with the article. In one preferred embodiment, as shown in FIG. 1, the article 20 may include an engaging member 70 extending laterally outwardly from each of the longitudinal edges 50 in the first waist region 36. However, as with the receiving member 60, the engaging member 70 may be disposed anywhere on the article so as to provide the intended fastening purpose. In at least one preferred embodiment, at least one receiving member 60 is disposed in the second waist region 38 and at least one engaging member 70 is disposed in the first waist region 36. In this configuration, the corresponding receiving member 60 and engaging member 70 can be fastened or engaged to form a closure and fasten the article 20 about the wearer, or provide a convenient means for disposal of the article 20.

The engaging member 70 may be the same or different in size, shape, material and/or construction as the first and second flaps 64 and 66 of the receiving portion 60. The engaging member may be separate pieces of material joined to the chassis 22 or may comprise a different portion or part of the article, such as the topsheet, backsheet, cuff material, waist member, etc. In any case, all or a portion of the engaging member 70 may be extensible, non-extensible or elastomeric. Again, a vacuum formed elastomer or other extensible and/or elastomeric/extensible material may be used. Further, the engaging member 70 may be at least partially breathable, and/or water vapor permeable, as well as liquid pervious or impervious.

Similar to the receiving member 60, the engaging member 70 of the fastening system 40 may form all or a portion of the primary fastening system and/or a secondary fastening system such as a disposal fastening system. As noted above, the disposal feature may be designed to provide a means for conveniently disposing of the article after use. In such cases, the engaging member 70 for the disposal feature may be the same as or different from any of the engaging member(s) 70 of the primary fastening system 40.

The engaging member 70 may include one or more fastening elements 72 to engage with the fastening elements 68 of the receiving member 60. The fastening elements may be disposed on at least a portion of one or more surfaces of the engaging member 70. The fastening elements 72 may comprise any known fastening means, such as hooks, loops, snaps, adhesive, cohesive, magnets, hermaphroditic fasteners, tab and slot fasteners, buckles or any combination of any of these or other fasteners. Further, the fastening elements 72 may be discrete pieces of material added to the engaging member 70 or may be integrally formed from the material making up all or a portion of the engaging member 70. As shown in FIG. 2, the fastening elements 72 may be substantially similar in size, shape and material to each other and may be disposed on one or more surfaces of the engaging member 70. Alternatively, the fastening elements 72 may be different from each other in type, shape, size, location and/or fastening characteristics. One example of an alternative embodiment is shown in FIG. 5 wherein the engaging member 70 includes a first surface 74 comprising a hook-type 80 fastening element 72 and a second surface 76 comprising a loop-type 82 fastening element 72. Another example is shown in FIG. 3 wherein the location of the fastening element 72 disposed on the first surface 74 is at least partially offset from the fastening element 72 disposed on the second surface 76. Although FIG. 3 shows the location of the fastening elements 72 offset in the lateral direction (i.e. parallel to the lateral centerline 110 of the article 20), the location of the fastening elements 72 can be varied in either or both the longitudinal or lateral directions, as desired.

The performance of the fastening system 40 of the present invention may be varied in order to optimize the performance of the fastening system 40 to a particular application. For example, the fastening system 40 may include different types of fastening elements 68 and/or 72 on one or more of the flaps 62 and/or engaging members 70, fastening elements 68 and/or 72 disposed on different locations of the one or more flaps 62 and/or engaging members 70, and/or different size fastening elements 68 and/or 72 disposed on the one or more flaps 68 and/or engaging members 70.

Regardless of whether similar type fastening elements 68 are used on the first and second flaps 64 and 66, the fastening characteristics of the fastening element 68 of the first flap 64 may be different from those of the fastening elements 68 of the second flap 66. For example, a fastening system including multiple loop and hook type fastening elements 68 may be configured such that at least one of the fastening elements 68 has different peel, shear or other fastening characteristics than one or more of the remaining fastening elements 68 when engaging with the fastening elements 72 of the engaging member. In one particular embodiment, for example, use of a hook fastener, such as an Aplix style 960e, in combination with a loop available from M&W (style# PK 6048.010) results in resistance to disengagement under shear load in excess of 5000 grams/inch. Other combinations may result in lower cost loop and or hook materials and, depending on the exact choice of loop and/or hook may be tailored to deliver varying shear load capability. For example, loop materials disclosed in U.S. Pat. No. 5,595,567 entitled "Nonwoven Female Component For Refastenable Fastening Device" and issued to King et al. on Jan. 21, 1997; U.S. Pat. No. 5,624,427 entitled "Female Component For Refastenable Fastening Device" and issued to Bergman et al. on Apr. 29, 1997; and U.S. Pat. No. 5,735,840 entitled "Disposable Diaper With Integral Backsheet Landing Zone" and issued to Kline et al. on Apr. 7, 1998, each of which is incorporated by reference, may be tailored to give a range of performance levels and a range of costs. For example, performance can be reduced to below 1000 grams/inch shear capability by changes in the type and basis weight of the nonwoven used, amount of strain, and type of hook.

FIG. 23 depicts a diaper 20 affixed on a wearer. The fastening system 40 preferably maintains the first waist region 36 and the second waist region 38 in a configuration so as to provide lateral tensions about the circumference of the diaper 20 to hold the diaper 20 on the wearer. FIG. 23 shows two axes, an x-axis generally oriented about the waist of the wearer and a y-axis generally oriented vertically on the wearer in a standing position. A z-axis is generally perpendicular to the x-axis and the y-axis and extends out of the plane of the figure. In one embodiment, the x-axis defines the primary direction of load bearing (i.e., lateral tensions about the circumference of the diaper around the waist of the wearer hold the diaper on the wearer).

In a diaper having surface fastening elements such as a hook and loop, hermaphroditic, adhesive, cohesive and/or magnetic fastening elements, the diaper is generally removed from the wearer by peeling the surface fastening elements away in the xz-plane such that the surface fastening elements are progressively disengaged by peeling in the xz-plane along the x-axis. Thus, the fastening system 40 preferably is not difficult to peel in the xz-plane so that the diaper may be easily removed from the wearer. Alternatively, at least a portion of the distal edge of a fastening element is preferably easier to remove in order to start the peeling action in the xz-plane. Thus, it is preferable that at least a portion of the distal edge of the fastening elements are not difficult to disengage in a peel mode by a force located substantially in the xz-plane for at least a portion of the engaged area of the fastening elements, however, the surface fastening system may become progressively more difficult to disengage as the peel mode disengagement progresses. When the wearer is active or when a diaper is pulled onto the wearer, the fastening system 40 will also preferably remain fastened in the presence of peel forces in directions other than in the xz-plane that are greater than the peel force that will disengage at least a portion of the fastening system 40 in the xz-plane.

FIG. 23 depicts axes y' and y" that are offset from the y-axis by an angle α on either side of the y-axis. In a preferred embodiment, the fastening system 40 is able to remain fastened when subjected to peel forces in all the planes between the y'z-plane and the y"z-plane, including the yz-plane when the peel forces greater than the peel force required to disengage the fastening system 40 in the xz-plane act on the fastening system 40. Preferably, the fastening system 40 is able to remain fastened when subjected to peel forces in a direction other than in the xz-plane, most preferably including the y'z-plane through the y"z-plane, that are greater than about 1000 grams, more preferably greater than about 1300 grams, even more preferably greater than about 1600 grams, and yet even more preferably greater than about 2000 grams. The angle α is preferably about 20 degrees, more preferably about 30 degrees, even more preferably about 40 degrees, yet even more preferably about 50 degrees and most preferably about 60 degrees. Preferably, however, at least a portion of the fastening elements of the fastening system 40 may become disengaged in a peel mode by a force oriented in the xz-plane that is less than the force that will cause the fastening system 40 to become disengaged in a peel mode by a force in a direction other than in the xz-plane, more preferably at least a portion of the fastening elements of the fastening system 40 may become disengaged in a peel mode by a force directed in the xz-plane less than or equal to about 1000 grams, even more preferably at least a portion of the fastening elements of the fastening system 40 may become disengaged in a peel mode by a force directed in the xz-plane less than or equal to about 750 grams, yet even more preferably at least a portion of the fastening elements of the fastening system 40 may become disengaged in a peel mode by a force directed in the xz-plane less than or equal to about 500 grams.

Many factors such as the ones described in copending U.S. patent application Ser. No. 09/633,422 filed on Aug. 7, 2000 by Mark J. Kline et al., which is incorporated by reference, may be used to optimize the fastening performance of the fastening system described herein in accordance with the desired performance requirements described above. For example, a fastening system 40 having hook and loop fastening elements may be designed to have a peel resistance greater than about 1000 grams in the yz-plane. In one particular embodiment, the fastening system 40 shown in FIG. 6 can include the hook fastening elements (3M # XPH-98112) on the engaging member 70 and loop fastening elements (3M # XPL-98237) on the receiving member 60. If the hook and loop fastening elements have a rectangular common engaged area of 0.5 inches in the x-direction and 1.5 inches in the y-direction, the fastening system 40 has been tested in accordance with the test method described below to have a peel resistance in the yz-plane in excess of 2100 grams.

The fastening system 40 may comprise an unbalanced system. Unbalanced systems may be more advantageous than balanced systems because the unbalanced systems may allow for greater optimization of cost and performance of the overall fastening system 40. An unbalanced system is one in which the connection between the first flap 64 of the receiving member 60 and the first surface 74 of the engaging member 70 in a closed configuration has at least some performance difference versus that of the connection between the second flap 66 of the receiving member 60 and the second surface 76 of the engaging member 70 in a closed configuration. The performance difference may be any related to differences in any of the following: one or more of the fastening elements 68 and 72 may vary in performance characteristics, technology type, size, shape or location relative to the in performance level, technology type, size, shape or location of one or more of the other fastening elements 68 and 72. For example, fastening system 40 may be unbalanced by offsetting the fastening elements 68 and 72 relative to each other, such as shown in FIG. 3.

Alternatively, fastening system 40 may be unbalanced by choosing the fastening element(s) 68 on the first flap 64 to have performance characteristics when joined to the fastening element(s) 72 on a first surface 74 of the engaging member 70 that are different than the performance characteristics of fastening elements(s) 68 on second flap 66 when joined to the second surface 76 of the engaging member 70. For example, in one particular embodiment of an unbalanced system, fastening elements 68 on the first flap 64 may be a nonwoven loop type fastener created by combining a nonwoven such as one available from BBA of Lewisburg, Pa. (style # L581.8) which is mechanically pre-strained and laminated to a pre-strained film available from Tredegar of Terre Haute, Ind. (style # X 25229) in a manner as described in U.S. Pat. No. 5,846,365 issued to Kline, et al on Dec. 8, 1998. When fastening element 72 on first surface 74 of engaging member 70 comprises a hook, such as 3M style # KN-0561, shear force capability of the system may only be about 500 grams/inch. If the previously mentioned Aplix 960e hook is used as fastening element 68 on second flap 66 and mates to an M&W loop style # PK 6048.010 on a second surface 76 of the engaging member 70, an unbalanced system is created because the shear force capability of the fastening elements 68 and 72 of one side of the system are about 500 grams/inch while the shear force capability of the second side of the system exceeds 5000 grams/inch. When performance characteristics between sides of the system are varied, any performance characteristic can be varied, including but not limited to shear force capability between fastening elements 68 and 72 and peel force to disengage fastening elements 68 and 72. In unbalanced systems in which the performance characteristics vary from side to side of the system, an "Unbalance Ratio" can be defined as the ratio between the performance level of the higher performing side to that of the lower performing side. Preferably, the unbalance ratio exceeds 1.1, more preferably exceeds about 1.25, even more preferably exceeds about 1.5, and most preferably exceeds 1.75. The higher performing side can be configured to be on the side closest to the surface of the wearer or on the side furthest away from the surface of the wearer.

Further, fastening system 40 may be unbalanced by using a different technology type on the fastening elements 72 on the first surface 74 of engaging member 70 relative to the technology type of the fastening elements 72 on the second surface 76 of engaging member 70. For example, first surface 74 fastening elements 72 may include a hook type fastener whereas second surface 76 fastening elements 72 includes a loop type fastener as shown in FIG. 5. Alternatively, first surface 74 fastening elements 72 may include an adhesive type fastener and second surface 76 fastening elements 72 may include a loop type fastener. Any variation of technology type between the first surface 74 fastening elements 72 and the second surface 76 fastening elements 72 is considered an unbalanced system.

Further, fastening system 40 may be unbalanced by using different sizes and/or shapes on the fastening elements 72 on the first surface 74 of engaging member 70 relative to the technology type of the fastening elements 72 on the second surface 76 of engaging member 70. For example, first surface 74 fastening elements 72 may be smaller in total length, width, or area than second surface 76 fastening elements 72. Any variation of in size or shape between the first surface 74 fastening elements 72 and the second surface 76 fastening elements 72 is considered an unbalanced system. When size varies, an "Unbalance Ratio" can be defined as the ratio between the size of the larger side to that of the smaller side. Preferably, the unbalance ratio exceeds 1.1, more preferably exceeds about 1.25, even more preferably exceeds about 1.5, and most preferably exceeds 1.75. The larger side may be configured to be on the side closest to the surface of the wearer or on the side furthest away from the surface of the wearer.

The receiving member 60 of the fastening system 40 may be disposed anywhere on the article 20. For example, the receiving member 60 may be disposed in the first waist region 36, the second waist region 38 or anywhere else on the article convenient to provide the article with the desired fastening function. Although the receiving member 60 may form a portion of the primary fastening system (i.e. the fastening system generally used to secure the article about the wearer during use), the receiving member 60 may also or alternatively form a portion of a disposal feature. As noted above, the disposal feature may be designed to provide a means for conveniently disposing of the article after use. In such cases, the disposal feature may include one or more receiving members 60 that are the same as or different from any of the receiving member(s) 60 of the primary fastening system 40.

In one embodiment, as shown in FIG. 1, a receiving member 60 is disposed in the second waist region 38 adjacent each longitudinal edge 50 of the article 20. The proximal portion 61 of each flap 62 is joined to the chassis 22 of the article and the distal portion 63 extends laterally outwardly from the proximal portion 61. The distal portion 63 of each flap 62 is not directly joined to any underlying portion of the article, and thus, is free to move or pivot about the location where the proximal portion 61 is joined to the chassis 22. Accordingly, in the embodiment shown, the distal portions 63 of the first flap 64 and the second flap 66 can be separated from their face-to-face closed configuration to a separated, open configuration, an example of which is shown in FIG. 2. In the open configuration, the flaps 62 of the receiving member 60 are separated and their inner surfaces 67 are exposed. It is in this open configuration that the flap fastening elements 68 are capable of accepting a corresponding engaging member 70.

Figure 8:
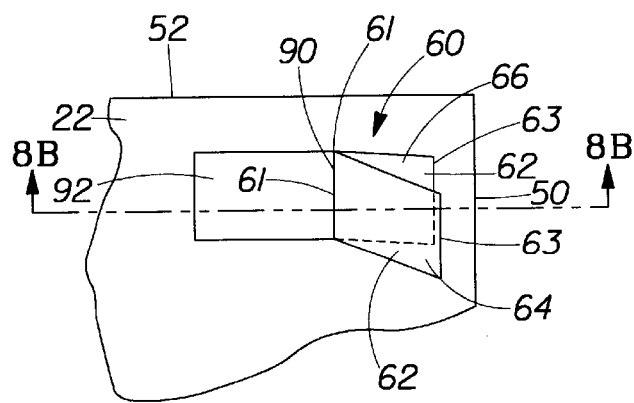
FIG. 8 is a partial plan view of an alternative embodiment of the fastening system of the present invention.
Figure 8A:
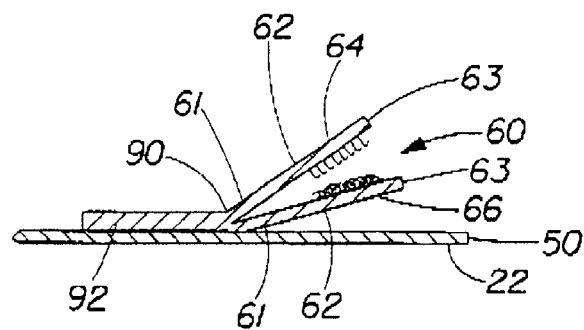
FIG. 8A is a cross-section of the article in FIG. 8 taken through section line B—B.

In another embodiment, as shown in FIGS. 8 and 8A, the receiving member 60 may comprise two or more flaps 62 joined along a hinge 90 to a base 92, which is in turn joined to the chassis 22 of the article 20 such as shown in FIG. 1. As shown in FIGS. 8 and 8A, the hinge 90 and the flaps 62 may be disposed completely inwardly of the lateral edge 52 or longitudinal edge 50 of the article 22. In other embodiments, however, at least a portion of the base 92, the hinge 90 or a portion of one or more of the flaps 62 may be located outwardly of the lateral edge 52 or longitudinal edge 50 of the article 20. In the embodiment shown in FIGS. 8 and 8A, the receiving member 60 includes a base 92 joined to the chassis 22 of the article 20 and two flaps 62, first flap 64 and second flap 66. The first and second flaps 64 and 66 may extend laterally and/or longitudinally outwardly from the base 92. Each of the flaps 62 may have a proximal portion 61 disposed adjacent to and joined with the base 92. When in a fastened configuration, the distal portion 63 of at least the first flap 64 is unjoined from the underlying structure of the article. The distal portion 63 of the second flap 66 may be unjoined to the structure of the article or may be partially or wholly joined to the chassis 22 by any known means. The first and second flaps 64 and 66 may be made from the same piece of material or different pieces which are joined to each other, to the base 92 and/or to the article.

Figure 7:
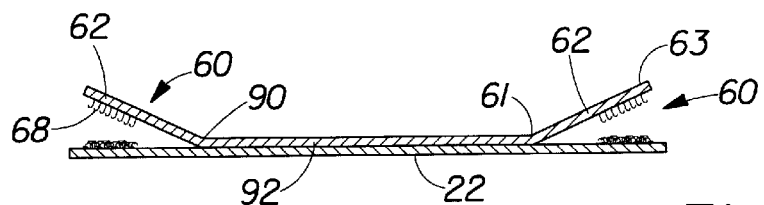
FIG. 7 is a cross-section of the article in FIG. 6 taken through section line A—A.

In yet another embodiment, the receiving member 60 may include a single flap 62 which has a proximal portion 61 joined to the chassis 22 of the article 20 and a distal portion 63 which extends from the proximal portion 61 and is unjoined to the underlying structure of the article. In such cases, the second flap 66 of some alternative embodiments may be replaced with a portion of the backsheet or another structure of the article 20 or a separate element joined to the article 20. One example of such an embodiment is shown in FIGS. 6 and 7. In FIGS. 6 and 7, the receiving member 60 includes a base 92 joined to the article 20 and one flap 62 extending laterally outwardly from the base 92 at each end of the material. (Although shown at lateral ends, the receiving member may extend from longitudinal ends.) In this particular embodiment, a single piece of material may form the base 92 and the flap 62 of at least two receiving members 60. Alternatively, each receiving member 60 may include a separate piece of material that includes a base 92 and a flap 62. It should be noted, however, that the piece(s) of material may include any number of pieces or layers that are joined together. The flaps 62 may be disposed apart from each other and may be separated by the base 92 of the material which is joined to the article, such as to the chassis 22.

In an alternative embodiment, the receiving member 60 may include a first flap 64 which is constructed from a portion of the underlying structure of the article 20, such as the backsheet 26. This configuration may be provided by cutting the backsheet 26 or other material to form the first flap 64. The hinge 90 of the flap 62 is that portion of the flap 62 which has not been cut or separated from the underlying material. The resulting opening in the backsheet or other material, or materials exposed by the opening can be configured to act as a fastening component in the fastening system 40, (e.g., to catch an engaging member 70) or a fastening element can be added to the article in the vicinity of the opening to provide the desired fastening function.

Figure 9:
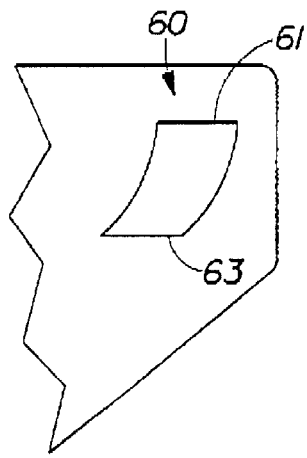
FIG. 9 is a partial plan view of an alternative embodiment of the fastening system of the present invention.
Figure 11:
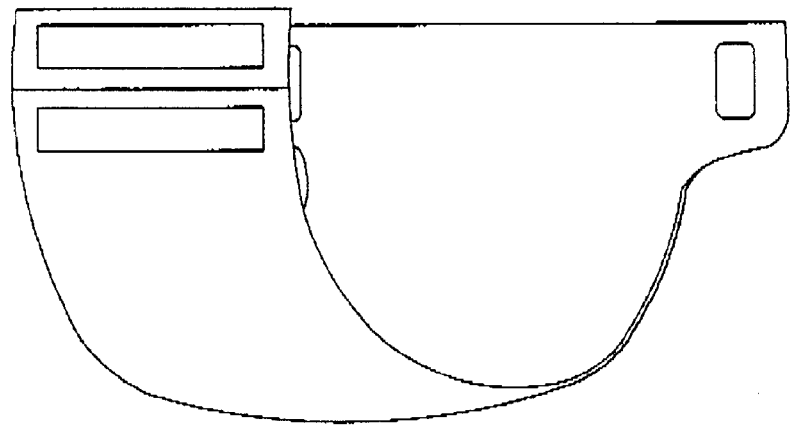
FIG. 11 is an isometric view of an absorbent article including an alternative embodiment of the fastening system of the present invention.
Figure 12:
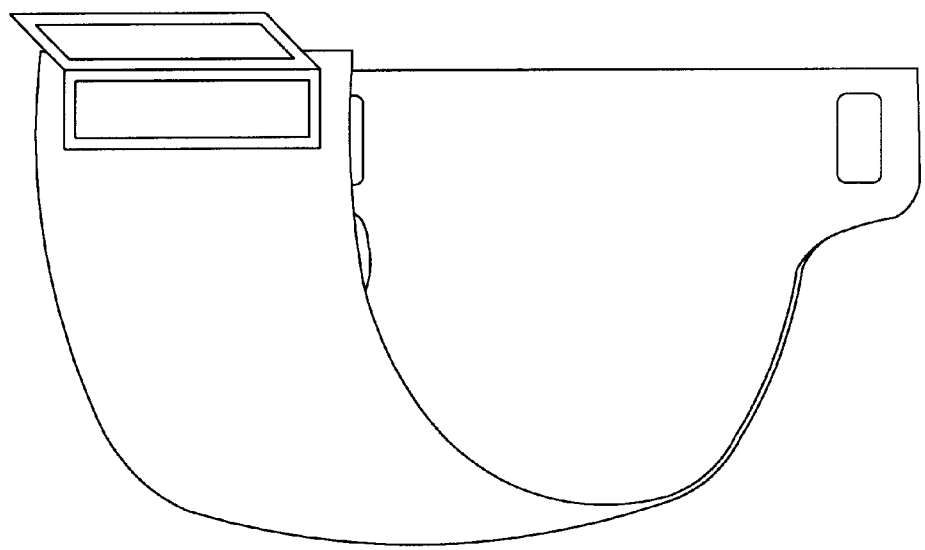
FIG. 12 is an isometric view of an absorbent article including an alternative embodiment of the fastening system of the present invention.

FIGS. 9, 11 and 12 show embodiments of the present invention wherein the hinge is oriented in a direction generally parallel to the primary direction of load bearing. In such configurations, the hinge 90 may be longitudinally inboard of the flaps 62 or may be longitudinally outboard of the flaps 62. In FIG. 9, for example, the hinge 90 is oriented in a direction generally parallel to the primary direction of load bearing 95 and is located longitudinally outboard of the flaps 62. FIGS. 11 and 12 show alternative embodiments of a receiving member having a hinge 90 oriented in a direction generally parallel to the primary direction of load bearing 95 and longitudinally outboard of the flaps 62. In the embodiment shown in FIG. 11, the hinge 90 is formed at the waist edge of the article 20, which may be folded away from the end edge 52 to form flap 62. The flap 62 may comprise a portion of the backsheet, the topsheet, a laminate including the backsheet and topsheet, or a material joined to the backsheet and/or the topsheet. FIG. 12 shows an alternative embodiment in which the receiving member includes a material or laminate of materials that is attached to the backsheet of the diaper. More specifically, a portion of the material or laminate of material may be attached to the backsheet to form a first flap 64, and a portion of the material or laminate that is not directly attached to the backsheet may form the second flap 66. The hinge 90 is formed at the connection of the first flap 64 to the second flap 66. Alternatively the first and second flaps 64 and 66 may each be free from the backsheet and joined to the backsheet along the hinge 90.

Figure 10:
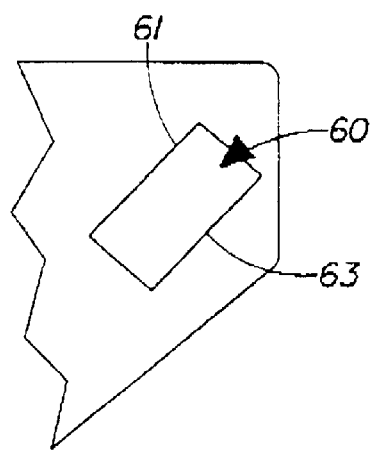
FIG. 10 is a partial plan view of an alternative embodiment of the fastening system of the present invention.

FIG. 10 shows an example of an embodiment of the present invention wherein the hinge 90 is oriented in a direction at an angle to the primary direction of load bearing 95. The flap fastening element 68 may also be oriented at an angle relative to the primary direction of load bearing. The hinge 90 may be oriented at the same or different angle as the flap fastening element 68. For example, the hinge 90 may be perpendicular to the primary direction of load bearing while the flap fastening element 68 may be oriented at an angle relative to the primary direction of load bearing. Alternatively, the hinge 90 may be at an angle relative to the primary direction of load bearing while the flap fastening element 68 may oriented perpendicular to the primary direction of load bearing. Any other combination is also possible. In any case, when viewing the product as affixed to the wearer from the wearer's front, if either is oriented at an angle to the primary direction of load bearing, preferably the lower edge is further inboard than the top. This may allow for the bottom of the flap fastener element 68 to be removed from an area likely to contact the thigh of the wearer and may prevent skin marking, while moving the top of flap fastener outboard may also allow for greater width of control of the waist regions near the edge of the product. However, the hinge 90 and/or the flap fastening element 68 may be oriented at any angle to the primary direction of load bearing, including angles which result in the bottom being further outboard than the top. The flap fastener element 68 may include more than one fastener sub-elements 68*a*, such as two or more patches of hook material or loop material. In such cases, the sub-elements form a "closure member major axis A" such as disclosed in U.S. Pat. No. 5,897,545, entitled "Elastomeric side panel for use with convertible absorbent articles" and issued to Kline, et al on Apr. 27, 1999 and is incorporated by reference herein. The closure member major axis A may be at any angle relative to the primary direction of load bearing, but preferably the closure member major axis A is angled such that when viewing the product as affixed to the wearer from the wearer's front, the laterally outboardmost edge of the longitudinally inboardmost fastener sub-element 68*a* is laterally inboard of the laterally outboardmost edge of at least one fastener sub-element 68*a* that is located more longitudinally outboard.

Figure 28:
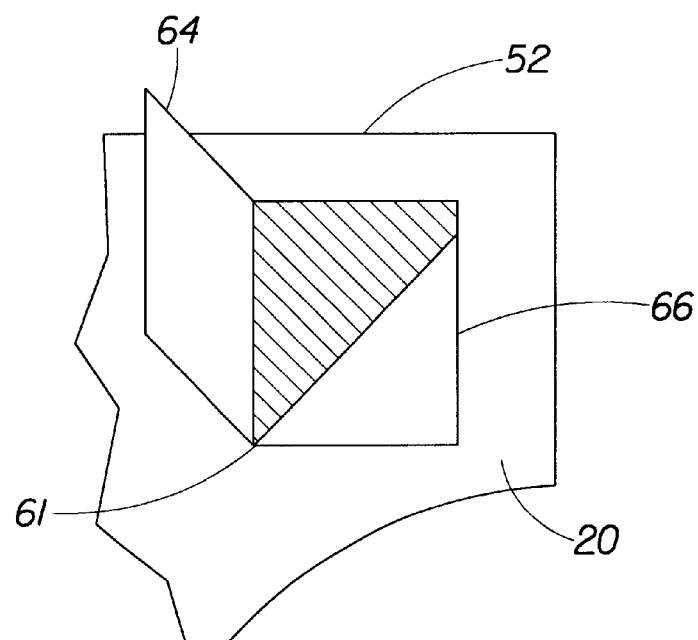
FIG. 28 is a partial perspective view of a fastening system of the present invention.

In an alternative embodiment of the invention, the fastening system 40 of the present invention may include a receiving member 60 such as shown in FIG. 28 that allows for reduced skin marking on the thigh of the wearer and allows for increased peel resistance. In this embodiment, the fastening system preferably includes a first flap 64 having a distal portion that is, at least in a fastened configuration, not joined to the underlying structure of the article 20, and a second flap 66 having at least a portion of the second flap 66 located outboard of the proximal edge 61 that is joined to the underlying structure of the article 20 and at least one of the distal corners of the second flap 66 that is, at least in a fastened configuration, not joined to the underlying structure of the article 20. Preferably, as shown in FIG. 28, the distal corner of the second flap that is located longitudinally inboard of the lateral edge 52 is not joined to the underlying structure of the article 20. In this embodiment the corner of the second flap 66, as well as the remainder of the fastening system 40, that is located adjacent to the leg of the wearer is able to move away or lift from the underlying structure of the article and out of the path of the leg of the wearer when the wearer moves his or her leg. In this way, the occurrence of skin marking due to the fastening system pressing against the leg of the wearer may be minimized. Additionally, allowing a corner or a lateral edge of the second flap 66 to move away or lift from the underlying structure of the article 20 may also increase the peel resistance to disengagement of the fastening elements of the fastening system 40. While not limiting to specific theory causing the increase, it is believed that this is because allowing the corner or lateral edge of the second flap 66 to lift can change the required mode of disengagement from peel mode disengagement to that of shear mode disengagement. Shear mode disengagement is disengagement via forces acting in the plane of the surface of the fastener, whereas peel mode disengagement results from forces acting generally perpendicular to the plane of the surface of the fastener. In many fasteners, such as hook and loop fasteners, it is generally more difficult to disengage the fasteners in shear mode than in peel mode. Thus, by creating a structure in a manner that causes forces acting upon the system to disengage via shear mode instead of peel mode disengagement, resistance to the disengagement of the fastener may be increased in one or more directions.

Figure 13:
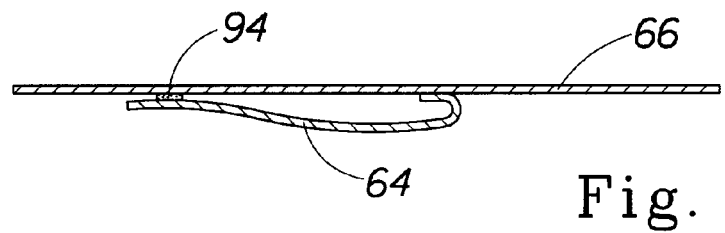
FIG. 13 is a partial cross-sectional view of an alternative embodiment of the fastening system of the present invention.
Figure 14:
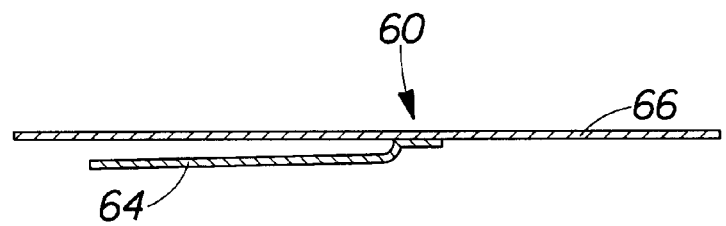
FIG. 14 is a partial cross-sectional view of an alternative embodiment of the fastening system of the present invention.
Figure 15:
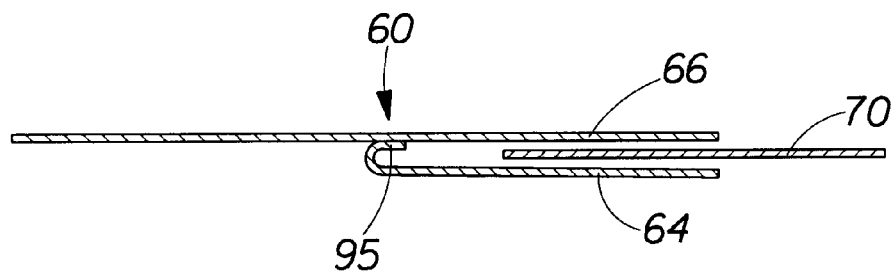
FIG. 15 is a partial cross-sectional view of an alternative embodiment of the fastening system of the present invention.
Figure 16:
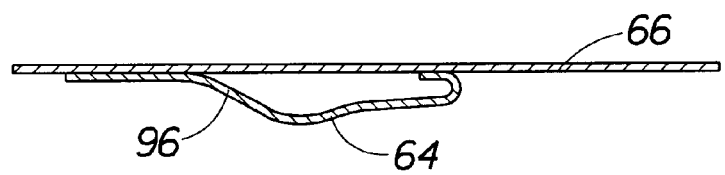
FIG. 16 is a partial cross-sectional view of an alternative embodiment of the fastening system of the present invention.

One or more of the flaps 62 of the receiving member 60 may also be folded away from one or more other flaps in a pre-fastened configuration such that the fastening element(s) 72 of the engaging member 70 may be more easily engaged with the flap fastening element(s) 68 of the one or more other flaps 62. FIGS. 13, 14 and 16, for example, show an embodiment in which a first flap 64 is folded away from a second flap 66 of the receiving member 60. After the second fastening element 73 of the engaging member 70 has been fastened to the fastening element 69 of the second flap 66, the first flap 64 may be folded back over the engaging member 70, bringing the fastening element 68 of the first flap 64 into contact with the first fastening element 72 and fastening the first flap 64 to the engaging member 70. The first flap 64 of the receiving portion 60 may be folded away from the second flap 66 and freely moveable towards the second flap 66, or the first flap 64 may be held away from the second flap 66. As shown in FIG. 14, for example, the first flap 64 may be joined to the second flap 66 in a configuration such that the natural position of the first flap 64 is directed away from the second flap 66 in an open configuration. FIG. 15 shows the receiving member 60 shown in FIG. 14 in a fastened configuration. In this configuration, the first flap 64 may be folded over a bond 95 in order to fasten the fastening element of the first flap 64 with the fastening element of the engaging member 70, or, in certain configurations, the first flap 64 and the second flap 66 may be made of a single material. Alternatively, the first flap 64 may be held away from the second flap 66 in a pre-fastened configuration by any mechanism, such as a mechanical bond, an adhesive or cohesive bond, a supplemental fastener such as a hook and loop, a snap, a magnet, a hermaphroditic fastener, a tab and slot, a buckle or any other type of fastener. FIG. 13, for example, shows the first flap 64 held away from the second flap 66 by a bond 94.

In yet another embodiment, the first flap 64 may also be held in place to a portion of the diaper 20 at a pre-weakened section such as a scored or perforated section. The first flap 64 may be removed by tearing the first flap 64 away from the diaper 20 at the pre-weakened section. For example, FIG. 16 shows one embodiment in which the first flap 64 is held away from the second flap 66 and attached to a portion of the diaper. In this embodiment, the first flap 64 may be released by tearing the first flap away at the score or perforation 96. Preferably, the holding mechanism allows for the first flap 64 to be freed from the diaper without damaging or tearing the first flap or the other portion of the diaper 20, except along a pre-weakened section of the first flap 64 or the diaper 20.

Figure 17:
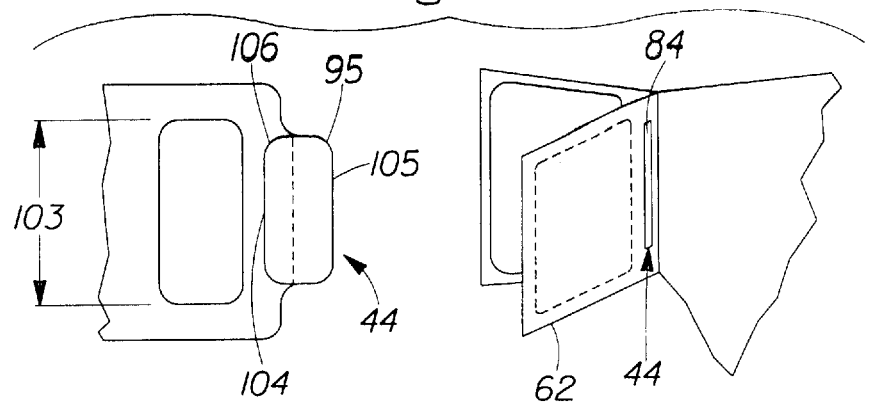
FIG. 17 is a partial plan view of a portion of one embodiment of a fastening system of the present invention.
Figure 18:
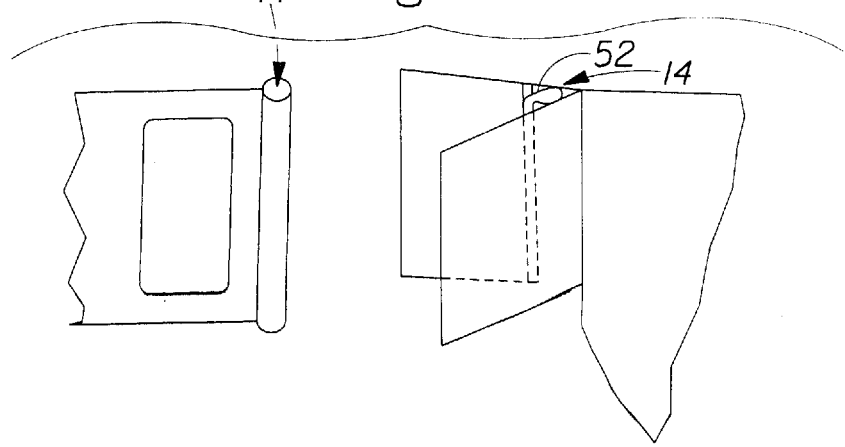
FIG. 18 is a partial plan view of a portion of one embodiment of a fastening system of the present invention.
Figure 19:
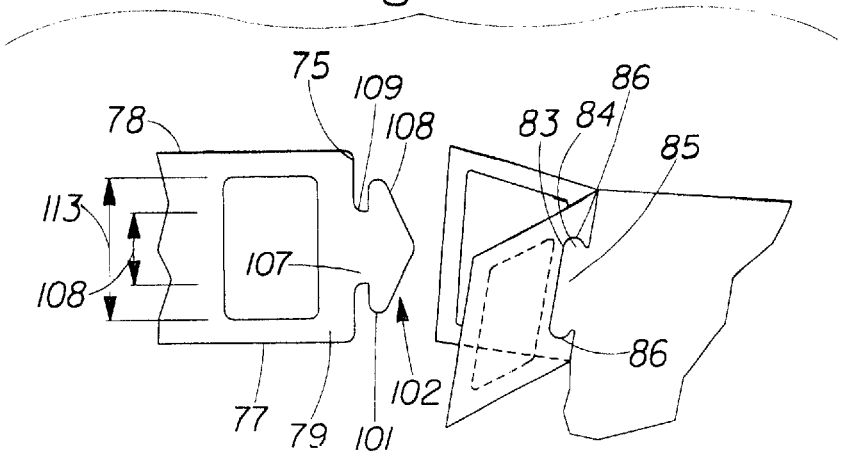
FIG. 19 is a partial plan view of a portion of one embodiment of a fastening system of the present invention.

As shown in FIGS. 17-19, the fastening system 40 of the present invention may also include a supplemental fastener 44 in addition to the primary fastener that includes the fastening elements 68 of the receiving member 60 and fastening elements 72 of the engaging member. The supplemental fastener 44 may include a different type of fastener than the primary fastener so that different benefits of the fasteners may be exploited. For example, a fastener having a high peel resistance may be used as a secondary fastener if the primary fastener has a high shear resistance, and, thus, the overall fastening system 40 may have both a high peel and a high shear resistance. The secondary fastener may include one or more of any known fastening means such as hooks, loops, snaps, adhesives, cohesives, magnets, tab and slot fasteners, interlocking projections and receptacles fasteners, buckles or any combination of these or other fasteners. A secondary fastener may also provide a means for vertically and/or horizontally aligning the primary fasteners located on the receiving member 60 and the engaging member 70.

In one particular embodiment, a fastening system 40 of the present invention may include an interlocking tab and slot fastener as a secondary fastener. In this embodiment, the receiving member 60 may include a slot or a tab, and the engaging member 70 may include a tab or a slot that engages with the slot or the tab of the receiving member 60, respectively. As shown in FIG. 17, for example, a receiving member may include a slot 84 disposed in one or more of the flaps 62, and the engaging member may include a tab 102 that may be passed through the slot 84 of the receiving member 60. The slot 84 includes an inboard edge 83 and an outboard edge 85. The inboard edge 83 of the slot 84 is located laterally inboard of the outboard edge 85 of the slot. The tab 102 includes a length 103, a proximal edge 104, a distal edge 105 and a lip portion 106. The tab 102 may be passed through the slot 84 to engage the interlocking tab and slot fastener of the fastening system 40. In a fastened configuration, at least the lip portion 106 of the tab 102 overlaps the outboard edge 85 of the slot 84 to prevent the tab 102 from disengaging the slot 84. Examples of tab and slot fasteners that may be used in a fastening system 40 of the present invention are described in detail in co-pending U.S. application Ser. No. 09/143,184 entitled "Absorbent Article Fastening Device" filed by Mark J. Kline et al. and assigned to the Procter & Gamble Company, which is incorporated by reference herein.

Figure 19A:
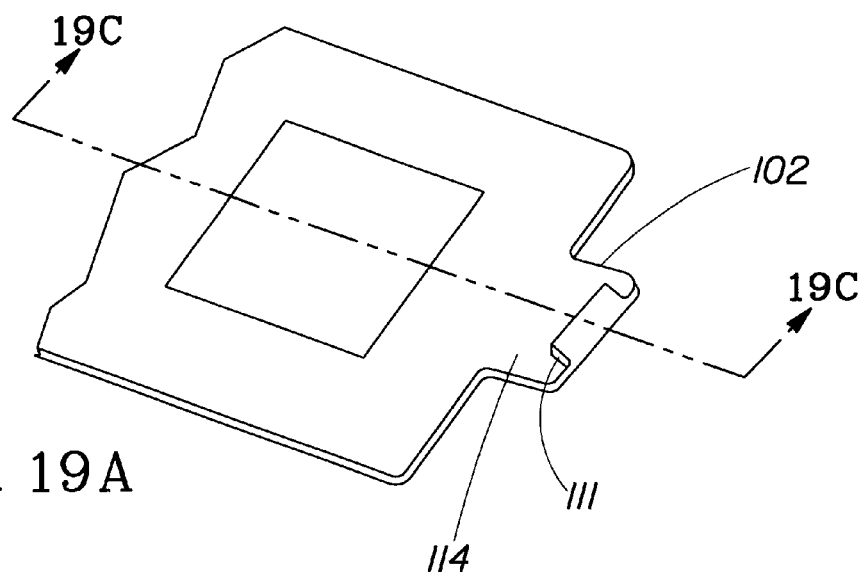
FIG. 19A is a partial perspective view of one embodiment of a fastening system of the present invention.
Figure 19B:
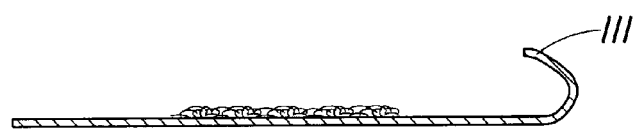
FIG. 19B is a cross-sectional view of the embodiment shown in FIG. 19A along section line 19B—19B.

FIG. 19 shows another embodiment of a tab and slot fastener that may be used as a secondary fastener in a fastening system 40 of the present invention. In this embodiment, the receiving member 60 may include a slot 84 such as shown and described in the example of FIG. 17. The slot 84 may have an inboard edge 83, an outboard edge 85, and two lateral edges 86. The engaging member 70 may include a tab having a neck portion 107 and a head portion 112. The neck portion 107 may be attached to the engaging member 70 along an edge of the engaging member 70 such as the distal edge 75, the proximal edge, the first lateral edge 78 or the second lateral edge 77. Alternatively, the neck portion 107 may be connected to the engaging member 70 on any portion of the first surface 74 or the second surface 76 of the engaging member 70. The neck portion 107 has a neck width 108 located adjacent to the head portion 112, and the head portion 112 has a head width 113 located adjacent to the neck portion 107. In one embodiment, such as the one shown in FIG. 19, the head width 113 may be greater than the neck width 108 so that the tab may include at least one lip 101 that extends beyond a lateral edge 109 of the neck portion 107. (FIG. 19 shows a tab embodiment including two lips 101.) Thus, when the tab 102 and slot 84 are in a fastened configuration, the at least one lip 101 of the head portion 112 may engage at least one of the lateral edges 86 of the slot 84 and prevent the tab 102 from being disengaged from the slot 84. As shown in FIGS. 19A and 19B, the tab 102 may include at least one flange 111 that extends laterally outwardly from the tab 102 and/or perpendicular to one or both of the faces 114 of the tab 102 and may engage at least one of the lateral edges 86, the inboard edge 83 and/or the outboard edge 85 of the slot 84 to prevent the tab 102 from being disengaged from the slot 84.

In yet another embodiment, the fastening system 40 of the present invention may include an interlocking projection and receptacle fastener as a secondary fastener. In this embodiment, the receiving member 60 may include a projection or a receptacle, and the engaging member 70 may include a projection or a receptacle that engages with the projection or receptacle of the receiving member 60, respectively. FIG. 18, for example, shows an embodiment in which the receiving member 60 includes a receptacle 54 positioned adjacent to the hinge 90 of the receiving member 60. The receptacle 54, however, may alternatively, or additionally, be located anywhere on one or more of the flaps 62. The engaging member 70 shown in FIG. 18 includes a projection 56 that may be slidably engageable with or may snap into the receptacle 54 of the receiving member 60. The receptacle 54 may further include a cap 58 or other form of stop on one or more of the ends of the receptacle 54 to prevent the projection from sliding beyond the cap. For example, the receptacle 54 may include a cap 58 on the bottom edge of the receptacle 54 so that the projection 56 may slide into the top edge of the receptacle 54 and may slide into the receptacle 54 until the bottom edge of the projection 56 comes into contact with the cap 58 on the bottom edge of the receptacle 54. The receptacle 54 may also include a cap 58 on both ends and the projection 56 may snap into the receptacle 54, and the caps may prevent the projection 56 from sliding out of the receptacle 54. In these embodiments, the fastening elements 72 of the engaging member 70 may be either or both horizontally and vertically aligned with the fastening elements 68 of the receiving member, thereby ensuring a proper contact of the fastening elements 68 and 72.

In certain embodiments the flap fastener elements 68 may be integral with the first flap 64 and/or second flap 66. Similarly, the fastening elements 72 of the engaging member 70 may be integral with the engaging member 70. For example, either the first flap 64, the second flap 66 or the engaging member 70 may be made of a fastening material, including but not limited to a loop material, a hook material, or a fastening tape. In certain preferred embodiments, at least a portion of the outer surface of the product may be a fastening material and may form at least one of the fastening elements 68 or engaging member fastening elements 72 of the fastening system 40. For example, the outer surface of an ear or a side panel may be made of a fastening material such as a hook or loop material and may form the engaging member 70. Exemplary loop-type materials suitable as integrated backsheet landing zones are disclosed in previously referenced U.S. Pat. No. 5,595,567 entitled "Nonwoven Female Component For Refastenable Fastening Device" and issued to King et al. on Jan. 21, 1997; U.S. Pat. No. 5,624,427 entitled "Female Component For Refastenable Fastening Device" and issued to Bergman et al. on Apr. 29, 1997; and U.S. Pat. No. 5,735,840 entitled "Disposable Diaper With Integral Backsheet Landing Zone" and issued to Kline et al. on Apr. 7, 1998.

In yet another embodiment, the receiving member 60 and/or the engaging member 70 may include at least an extensible portion and preferably an elastomeric portion. The extensible or elastomeric portion may be on one or both flaps 62 of the receiving member 60, and preferably the extensible and/or elastomeric portion is located laterally inboard of flap fastening elements 68 such that once the engaging member 70 and receiving member 60 are configured in a wearing configuration, the extensible and/or elastomeric portion is free to extend and/or contract after being extended and conform to the wearer as the wearer moves. Similarly, if the extensible and/or elastomeric portion is on the receiving member 60, preferably it is located laterally inboard of fastening elements 72 such that once the engaging member 70 and receiving member 60 are configured in a wearing configuration, the extensible and/or elastomeric portion is free to extend and/or contract after being extended and conform to the wearer as the wearer moves.

In yet other preferred embodiments, the flaps 62 of receiving member 60 may form separate waist and thigh panels as described in U.S. Pat. Nos. 6,004,306 and 5,997,521 issued to Robles and published application WO 95/13775 in the name of Don Roe, each of which is incorporated by reference. The waist and thigh panels may be inextensible, extensible, or elastomeric. Most preferably, at least one panel, the waist or the thigh panel, is elastomeric. In any case, if the flaps 62 form waist and thigh panels, the fastening elements 72 of engaging member 70 mate with flap fastener elements 68 on the waist panel flap 62 and thigh panel flap 62 as described already herein to secure the first waist region to the second waist region. In such embodiments, the locations at which the flaps attach to the article may occupy at least a portion of the same longitudinal or lateral space or may not share any common longitudinal or lateral space. Thus, the location the first flap 64 is joined to the article may be at least partially laterally and/or longitudinally offset from the location the second flap 66 is joined to the article. In any case, in embodiments which include waist and thigh panels, preferably receiving member 60 is attached to the waist region of the product intended to be placed against the back waist of the wearer's body.

In other preferred embodiments, the product may be delivered to the consumer at least partially pre-fastened. For example, flap fastening elements 68 of at least one flap 62 of at least one receiving member 60 may be joined with fastening elements 72 of at least one engaging member 70 during the article's manufacture. Preferably, flap fastening elements 68 of first flap 64 are joined with fastening elements 72 on first surface 74 of engaging member 70 and flap fastening elements 68 of second flap 66 are joined with fastening elements 72 on second surface 76 of engaging member 70 during the article's manufacture. Prefastening of the product during its manufacture allows the consumer to slip the product over the wearer's feet and pull it in place about the torso as one does a traditional pull on article. Yet, the fasteners enable the user to disengage the fasteners if they so choose and fasten the article about the wearer without needing to remove lower body clothing, such as pants, stockings, or shoes.

Figure 20:
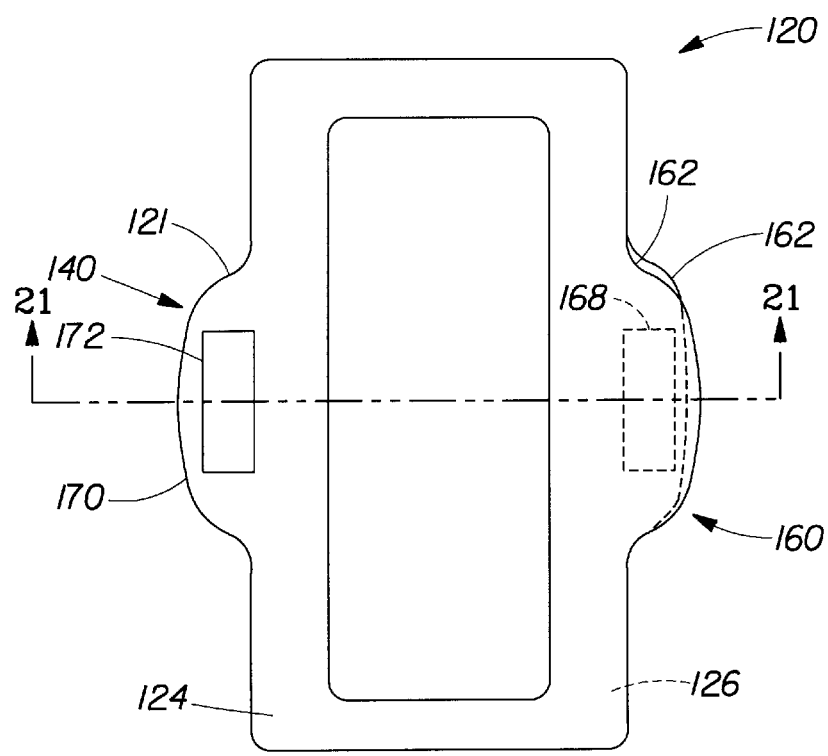
FIG. 20 is a plan view of a sanitary napkin embodiment including the fastening system of the present invention.
Figure 21:
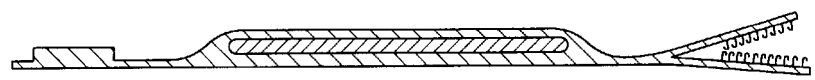
FIG. 21 is a cross-sectional view of the article shown in FIG. 15 taken through section line C—C.

FIGS. 20 and 21 show an example of an alternative embodiment of the present invention such as a sanitary napkin or light incontinent pad that includes the fastening system 140 of the present invention to hold the sanitary napkin or light incontinent pad in a configuration wrapped around a wearer's panties or underwear. For example, the fastening system 140 may be used to fasten wings 121 of a sanitary napkin 120 about a wearer's panties. Fastening the wings 121 of a sanitary napkin about the wearer's undergarment may help ensure that the sanitary napkin 120 will stay in place while in use and provides a means for reducing the likelihood that the undergarment will be soiled if the core of the sanitary napkin 120 should leak. The fastening system 140 of the sanitary napkin 120, for example, may include a receiving portion and an engaging portion. As shown in FIGS. 20 and 21, for example, the receiving member 160 and the engaging member 170 may extend outwardly from the longitudinal edge 150 of the sanitary napkin 120. Alternatively, the receiving member 160 or the engaging member 170 may be disposed on a portion of the backsheet 126 or topsheet 124 of the sanitary napkin 120 in a configuration similar to any of the embodiments described above with respect to a diaper and/or shown in FIGS. 6 through 11. As described above with respect to other embodiments of the present invention, one or more of the flaps 162 of the receiving member 160 may include one or more flap fastening elements 168 disposed one or more surface of the one or more flaps 162, and the flap fastening elements 168 may comprise any known fastening means, such as hooks, loops, snaps, adhesive, cohesive, magnets, tab and slot fasteners, buckles or any combination of any of these or other fasteners. The receiving member 160 and/or the engaging member 170 may also include any of the embodiments described above with respect to the fasteners shown in FIGS. 1 through 14. Additionally, flap fastening elements 168 of at least one flap 162 of at last one receiving member 160 may be joined with fastening elements 172 of at least one engaging member 170 during the article's manufacture. Preferably, flap fastening elements 168 of first flap 164 are joined with fastening elements 172 on first surface 174 of engaging member 170 and flap fastening elements 168 of second flap 166 are joined with fastening elements 172 on second surface 176 of engaging member 170 during the article's manufacture. Although the fastening system 140 is shown in FIG. 20 as the primary fastening device, the fastening system 140 of the present invention may be used in conjunction with other means for securing the napkin to the undergarment or around the undergarment such as adhesives, cohesives, mechanical fasteners, buttons, snaps, friction, static, magnets, and/or any other means known in the art. The fastening system 140 may also be used to fasten the sanitary napkin 120 to other devices such as belts or other sanitary guards, or may be used as a means for wrapping the sanitary napkin 120 in a disposal configuration. Examples of sanitary napkins with which the fastening system 140 of the present invention may be used are described in detail in U.S. Pat. No. 5,267,992 entitled "Shaped Sanitary Napkin With Flaps" issued to Van Tilburg on Dec. 7, 1993, and U.S. Pat. No. 5,389,094 entitled "Absorbent Article Having Flaps and Zones of Differential Extensibility" issued to Lavash et al. on Feb. 14, 1995, each of which is incorporated by reference herein.

Figure 22:
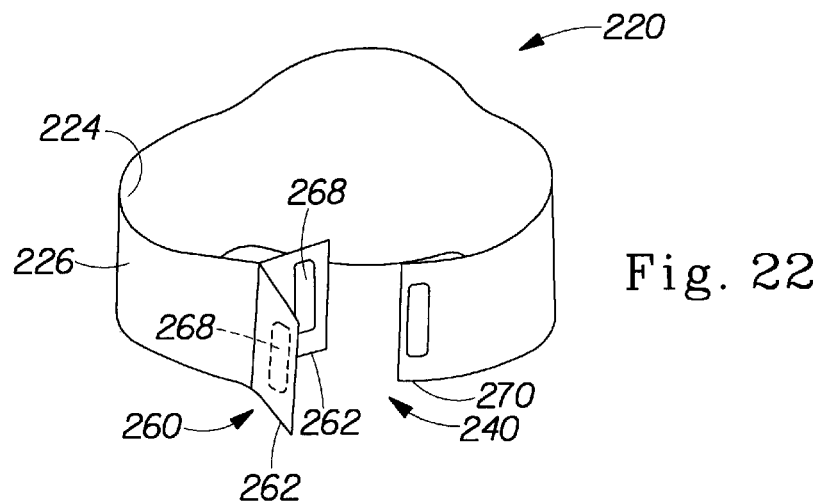
FIG. 22 is a body wrap article including one embodiment of the fastening system of the present invention.

In yet another embodiment, a body wrap may include a fastening system 240 of the present invention to hold the body wrap in a fastened configuration around a portion of a wearer's body such as around the wearer's waist, torso, leg, ankle, foot, arm, wrist, hand, neck, head, etc. FIG. 22, for example, shows one possible embodiment of a body wrap 220 of the present invention having a fastening system 240 including a receiving portion and an engaging portion. The receiving member 260 and the engaging member 270 may extend outwardly from an end edge 250 of the body wrap 220. Alternatively, the receiving member 260 and/or the engaging member 270 may be disposed on a portion of the an inner surface 224 or an outer surface 226 of the body wrap 220 in a configuration similar to any of the embodiments described above with respect to a diaper or sanitary napkin and/or shown in the Figures. One or more of the flaps 262 of the receiving member 260 may include one or more flap fastening elements 268 disposed one or more surface of the one or more flaps 262, and the flap fastening elements 268 may comprise any known fastening means, such as those described above. Further, the receiving member 260 and/or the engaging member 270 may also include any of the embodiments described above with respect to the fasteners shown in FIGS. 1 through 16. Examples of body wraps with which the fastening system 240 of the present invention may be used are described in detail in U.S. Pat. No. 5,741,318 entitled "Elastic Back Wrap Having Diamond-Shaped Thermal Pattern and Anti-slip Means" issued to Oullette et al. on Apr. 21, 1998, and U.S. Pat. No. 5,860,945 entitled "Disposable Elastic Thermal Knee Wrap" issued to Cramer et al. on Jan. 19, 1999, each of which is incorporated by reference herein.

Test Methods

T-Peel Strength Method

The peel mode disengagement force is determined according to the method described below, which is an adaptation of ASTM Designation D5170-91, "Standard Test Method for Peel strength ("T" method) of hook and loop touch fasteners." Other references relevant to running the peel mode disengagement force test using tensile testing machines include ASTM Designation D 76, "Specifications for Tensile testing Machines for Textiles," and ASTM Designation E 4, "Standard Practice for verification of Testing Machines." This method is intended for determining the relative peel resistance of a surface fastening system by means of a T-type specimen. T-Peel is the load to produce progressive separation of two bonded, flexible adherents.

The test method can be used to measure peel mode disengagement from a direction other than the primary direction of load bearing (such as could occur during pull-on or wearing of the product) or in the primary direction of load bearing (such as when removing the product)

Apparatus

The following apparatuses are used: a Constant rate of extension Tensile Tester, Jaws, Scissors, a Load Cell and an eleven pound (11 lb.) hand operated roller. The Constant rate of extension Tensile Tester is a universal constant rate of extension tensile testing machine that complies with the requirements of ASTM D76. The Jaws include two clamps with centers in the same plane, parallel to the direction of the motion of the stressing clamp, and so aligned that they will hold the specimen ends wholly in the same plane. The faces must be wide enough to include the entire specimen. In the test, a load cell is selected so that the tensile results for the strip tested will be between 20% and 80% of the load range used. The load cell preferably meets the specification of ASTM Designation E-4. The eleven pound (11 lb.) hand operated roller is a steel roller measuring 82.6 mm (3.35 inch)±2.5 mm (0.1 inches) diameter, 44.4 mm (1.75 inch) ±1.3 mm (0.05 inches) in width, covered with rubber approximately 6.4 mm (0.25 inches) in thickness and having Shore scale A durometer hardness of 80±5. The surface of the roller shall be a true cylinder void of any concave or convex deviations. The mass of the roller is 11 lbs.±0.1 lb.

Facilities

For the purposes of this test method, a conditioned room refers to a room controlled to 23.0°±1.0° C. (73.4°±1.8° F.) and 50%±2% relative humidity.

Preparation and Calibration of Instruments

The instruments are prepared and calibrated by the following steps:

(1) Calibrate the tensile tester according to manufacturer's instructions. Choose a Load Cell so that tensile results for the strip tested will be between 20% and 80% of the load range used.
(2) Set the gage length to 38 mm (1.5 inches).
(3) Set the instrument crosshead to operate at 254 mm/minute (10.0 inches/minute).
(4) If the tensile tester is computer interfaced, set the program to mark the Peak Load.

Sample Preparation

For testing peel in other than the primary direction of load bearing, the sample to be tested is prepared according to the following steps:

(1) Determine if peel mode is possible from the direction to be measured. If peel mode is not possible, the result is recorded as "infinite peel" and no testing occurs. For example, peel mode is not possible from the yz-plane on constructions shown in FIG. 24-27 because hinges 91 and 93 protect engaging member 70 from peel in the yz-plane from either longitudinal edge. However, peel in the yz-plane is possible on constructions shown in FIGS. 1,2,6-12 17-19,21-23, and 28.
(2) Condition samples a minimum of two hours prior to testing, according to conditions stated in the facilities section of this method.
(3) Attach a first leader to the engaging member. The leader should extend about 3 inches from the edge of the fastener in the y-direction (or direction other than the primary direction of load bearing to be measured) and be about the same width as the widest portion of the fastening system. The leader should be an extension of the material on which the fastener is mounted on the product. If this is not possible, a suitable material should be chosen with similar modulus and bending stiffness as the material on which the fastener is mounted on the article.
(4) Attach a second leader to the receiving member structure. The leader is attached to the second flap if the second flap extends from an edge of the article. Otherwise, the leader is attached to the underlying structure of the article, with any flaps and/or fastening elements attached to the underlying structure as intended in the product. The leader should extend about 3 inches from the edge of the fastener in the y-direction (or direction other than the primary direction of load bearing to be measured) and be about the same width as the widest portion of the fastening system. The leader should be an extension of the material on which the fastener is mounted on the product, such as the flap or underlying structure of the article as discussed immediately above. If this is not possible, a suitable material should be chosen with similar modulus and bending stiffness as the material on which the fastener is mounted on the article.
(5) Lay the engaging member on top of the receiving member such that their edges align as intended when fastened in a configuration for use of the product and fold any flaps of the receiving member into a closed position, as intended for use. Using the 11 pound roller, roll the combined engaging and receiving member over the area including the fastening elements, rolling four times in the same direction without applying additional weight to the roller, at a velocity of 305 mm per minute (12 inches per minute). Note: An automated mechanical roller may be substituted for the hand-roller but must perform the above described rolling action.

For testing peel in the primary direction of load bearing, the sample to be tested is prepared according to the following steps:

(1) This direction of peel is primarily intended to represent intentional removal of the product, so the sample is prepped to peel apart individual layers of the receiving member and engaging member until the engaging member and receiving member are completely disengaged. Thus, multiple tests will occur to peel all layers apart from each other. For example, first flap 64 fastening elements 68 of FIG. 2 would be peeled from engaging member 70 fastening elements 72 in a first xz-direction (from the distal end of the first flap 64 toward the proximal end of the first flap 64). Then, engaging member 70 fastening elements 72 would be peeled from second flap 66 fastening elements 68 in a second xz-direction, opposite of the first xz-direction (that is, from the distal end of the engaging member 70 toward the proximal end of the engaging member 70). If a flap includes a hinge line substantially parallel to the primary direction of load bearing (as shown in FIGS. 9, 11, 12, and flaps 64 and 64 of FIGS. 24 and 26), that layer is not tested. Thus only layers which can be peeled in the primary direction of load bearing are tested.

(2) Condition samples a minimum of two hours prior to testing, according to conditions stated in the facilities section of this method.

(3) Attach a first leader to the first portion of the fastener to be peeled from a second portion of the fastener. Depending on which layers are being peeled, the first portion could, for example, be a flap of the receiving member or the engaging member. The leader should extend about 3 inches from the edge of the fastener in the x-direction from the edge peel is intended to be initiated and be about the same width as the widest portion of the fastening system. The leader should be an extension of the material on which the fastener is mounted on the product. If this is not possible, a suitable material should be chosen with similar modulus and bending stiffness as the material on which the fastener is mounted on the article.

(4) Attach a second leader to the second portion to be peeled from the first portion. Depending on which layers are being peeled, the second portion could be, for example, an engaging member, a flap of the receiving member, or the underlying structure of the article. If the article includes a second flap extending from an edge of the article and the layers being peeled are the engaging member from the second flap, the leader is attached to the second flap. In any other case in which the layers being peeled are the engaging member from the second flap (or second receiving fastening elements in constructions in which there is no second flap), the leader is attached to the underlying structure of the article, with any flaps and/or fastening elements attached to the underlying structure as intended in the product. The leader should extend about 3 inches from the edge of the fastener in the x-direction from the edge peel is intended to be initiated and be about the same width as the widest portion of the fastening system. The leader should be an extension of the material on which the fastener is mounted on the product, such as the flap or underlying structure of the article as discussed immediately above. If this is not possible, a suitable material should be chosen with similar modulus and bending stiffness as the material on which the fastener is mounted on the article.

(5) Lay the first portion on top of the second portion such that their edges align as intended when fastened in a configuration for use of the product. Using the 11 pound roller, roll the combined first and second portions over the area including the fastening elements, rolling four times in the same direction without applying additional weight to the roller, at a velocity of 305 mm per minute (12 inches per minute). Note: An automated mechanical roller may be substituted for the hand-roller but must perform the above described rolling action.

Procedure

The test procedure is performed according to the following steps:

(1) Calibrate the instrument according the manufacturer's instruction.

(2) Insert first leader into the bottom clamp such that about 0.75 inch of the leader (½ the gage length) is between the bottom clamp and the first edge of the connected sample, close the clamp.

Figure 29:
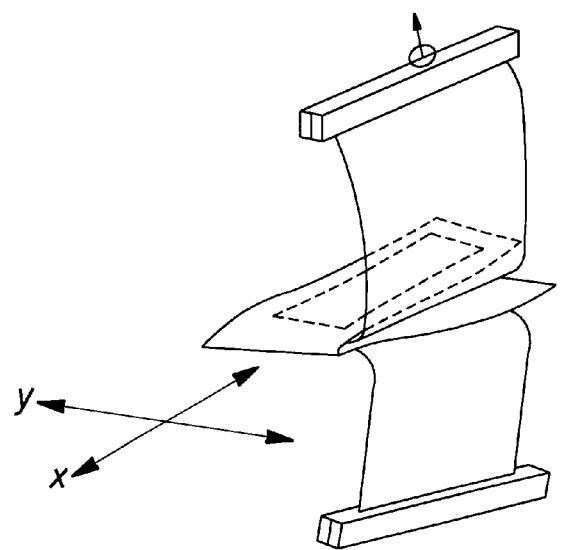
FIG. 29 is a perspective view of an exemplary fastening system of the present invention being tested according to the test method described herein.
Figure 30:
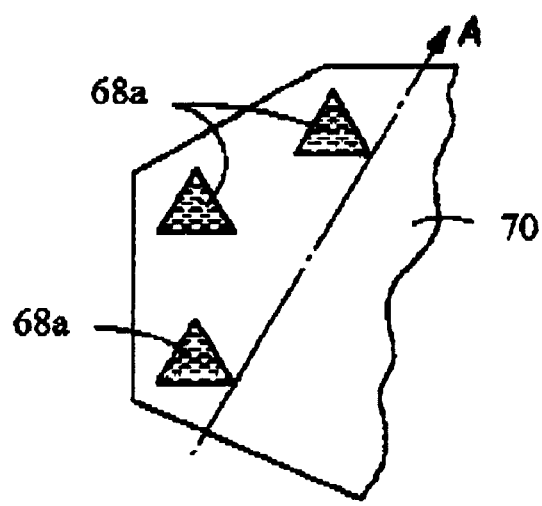
FIG. 30 is a partial view of an exemplary ear panel and the engaging components joined thereto.

(3) Insert second leader into the top clamp such that about 0.75 inch of the leader (½ the gage length) is between the top clamp and the first edge of the connected sample with enough tension not to exceed 5 grams of force. The first edge of the connected sample should be about midway between the top and bottom clamps and ready to test. The sample should look as shown in FIG. 29 at this point.

(4) Start the tensile tester, collect data throughout the peel.

(5) When the specimen is completed return the crosshead to its original starting point (gage length).

Calculations

To calculate the Peak Load, read the load in Newtons from the curve/data. The Peak Load is the highest point on the curve/data.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An article to be worn about a wearer comprising:
   an unbalanced fastening system joined to the article including
      a receiving member having at least a first receiving fastening element and a second receiving fastening element, the first receiving fastening element being disposed on a flap having a proximal portion joined to the article and a distal portion extending from the proximal portion, the second receiving fastening element being disposed so as to be generally in face to face relationship with the first receiving fastening element when the receiving member is in a closed configuration; and
      an engaging member having at least a first engaging fastening element and a second engaging fastening element disposed thereon, the first engaging fastening element being engageable with at least the first receiving fastening element and the second engaging fastening element being engageable with at least the second receiving fastening element,
      wherein said unbalanced fastening system is characterized in that a first connection between said first receiving fastening element of said receiving member and said first engaging fastening element of said engaging member in a closed configuration has at least some performance difference versus that of a second connection between said second receiving fastening element of said receiving member and said second engaging fastening element of said engaging member in a closed configuration.

2. The article of claim 1, wherein the first receiving fastening element is a different type of fastener from the second receiving fastening element.

3. The article of claim 1, wherein the first receiving fastening element includes hooks and the first engaging fastening element includes loops.

4. The article of claim 1, wherein the first receiving fastening element includes loops and the first engaging fastening element includes hooks.

5. The article of claim 1, wherein the first receiving fastening element includes hooks and the first engaging fastening element includes hooks.

6. The article of claim 1, wherein the fastening system is unbalanced in one or more of the group of: performance characteristics of one or more fastening element, technology type of one or more fastening element, size, shape and location.

7. The article of claim 1, wherein the flap includes a hinge.

8. The article of claim 1, wherein at least a portion of the flap is selected from one or more of the group of: extensible and elastomeric.

9. The article of claim 1, further comprising a second flap having a second proximal portion joined to the article and a second distal portion extending from the second proximal portion, the second receiving fastening element being disposed on the second flap so as to be generally in a face to face relationship with the first receiving fastening element when the receiving member is in a closed configuration.

10. The article of claim 9, wherein the flap and the second flap extend outward from an edge of the article.

11. The article of claim 9, wherein the second flap is made from a portion of one or more of the group selected from: a topsheet and a backsheet.

12. The article of claim 9, wherein the flap and the second flap include a hinge.

13. The article of claim 12, wherein the hinge of the second flap is oriented in a different direction relative to the hinge of the flap.

14. The article of claim 9, wherein the hinge may be oriented in a direction selected from one of the group of: substantially perpendicular to a primary direction of load bearing, substantially parallel to a primary direction of load bearing or at an angle between substantially perpendicular to and substantially parallel to a primary direction of load bearing.

15. The article of claim 1, wherein the article is an absorbent article and the flap is made from a portion of one or more of the group selected from: a topsheet and a backsheet.

16. The article of claim 1, wherein the flap is joined to a belt of the article.

17. The article of claim 1, wherein the first receiving fastening element and the second receiving fastening elements are laterally offset.

18. The article of claim 1, wherein the first receiving fastening element and the second receiving fastening elements are longitudinally offset.

19. The article of claim 1, wherein the fastening system includes a secondary fastener member.

20. The article of claim 19, wherein the secondary fastener member includes one or more from the group selected from: a tab and slot fastener, an interlocking projection and receptacle fastener, a snap, a hook, a loop, an adhesive, a cohesive, a magnet and a buckle.

21. The article of claim 1, wherein the distal portion of the flap is joined to the article in an open configuration prior to use.

22. The article of claim 1, wherein the flap is held in an open configuration on the article prior to use via one or more of the group selected from: a perforation, score, bond and slit.

23. The article of claim 1, wherein the article is one or more of the group selected from: an absorbent article, a disposable diaper, a sanitary napkin and a body wrap.

24. The article of claim 1, wherein the engaging member is at least partially extensible or elastic.

25. The article of claim 1, wherein a closure member major axis of at least one of the fastening elements is oriented at an angle to a primary direction of load bearing.

26. The article of claim 25, wherein the fastening element is a hook.

27. The article of claim 1, wherein the fastening system of the article is pre-fastened.

28. The article of claim 27, wherein the fastening system has a peel resistance in the primary direction of load bearing less than the peel resistance in a direction other than the primary direction of load bearing.

29. An article to be worn about a wearer comprising:
an unbalanced fastening system joined to the article including
a receiving member having at least a first receiving fastening element and a second receiving fastening element, the first receiving fastening element being disposed on a flap having a proximal portion joined to the article and a distal portion extending from the proximal portion, the second receiving fastening element being disposed so as to be generally in face to face relationship with the first receiving fastening element when the receiving member is in a closed configuration; and
an engaging member having at least a first engaging fastening element and a second engaging fastening element disposed thereon, the first engaging fastening element being engageable with at least the first receiving fastening element and the second engaging fastening element being engageable with at least the second receiving fastening element,
wherein the fastening system has a primary direction of load bearing and has a peel resistance in a direction other than the primary direction of load bearing greater than or equal to about 1000 grams.

30. The article of claim 29, wherein the fastening system has a peel resistance in the primary direction of load bearing less than the peel resistance in a direction other than the primary direction of load bearing.

31. An article to be worn about a wearer comprising:
a fastening system joined to the article including
a receiving member having at least a first receiving fastening element and a second receiving fastening element, the first receiving fastening element being disposed on a flap having a proximal portion joined to the article and a distal portion extending from the proximal portion, the flap being substantially unjoined to the article, the second receiving fastening element being disposed on a second flap so as to be generally in face to face relationship with the first receiving fastening element when the receiving member is in a closed configuration, the second flap being substantially unjoined to the article; and
an engaging member having at least a first engaging fastening element and a second engaging fastening element disposed thereon, the first engaging fastening element being engageable with at least the first receiving fastening element and the second engaging fastening element being engageable with at least the second receiving fastening element, wherein the fastening system has a primary direction of load bearing and has a peel resistance in a direction other than the primary direction of load bearing greater than or equal to about 1000 grams.

32. An article to be worn about a wearer comprising:

a fastening system joined to the article including a receiving member having at least a test receiving fastening element and a second receiving fastening element, the first receiving fastening element being disposed on a flap having a proximal portion joined to the article and a distal portion extending from the proximal portion, the second receiving fastening element being disposed so as to be generally in face to face relationship with the first receiving fastening element when the receiving member is in a closed configuration; and an engaging member having at least a first engaging fastening element and a second engaging fastening element disposed thereon, the first engaging fastening element being engageable with at least the first receiving fastening element and the second engaging fastening element being engageable with at least the second receiving fastening element;

wherein the fastening system has a primary direction of load bearing and has a peel resistance in a direction other than the primary direction of load bearing greater than or equal to about 1000 grams.

33. The article of claim 32, wherein the fastening system has a peel resistance in a direction other than the primary direction of load bearing greater than or equal to about 1300 grams.

34. The article of claim 32, wherein the fastening system has a peel resistance in a direction other than the primary direction of load bearing greater than or equal to about 1600 grams.

35. The article of claim 32, wherein the fastening system has a peel resistance in a direction other than the primary direction of load bearing greater than or equal to about 2000 grams.

36. The article of claim 32, wherein the fastening system has a peel resistance in the primary direction of load bearing less than the peel resistance in a direction other than the primary direction of load bearing.

37. The article of claim 32, wherein the direction other than the primary direction of load bearing includes at least the range from an angle 70 degrees from the primary direction of load hearing to an angle 110 degrees from the primary direction of load bearing.

* * * * *

UNITED STATES PATENT AND TRADEMARK OFFICE
CERTIFICATE OF CORRECTION

PATENT NO. : 6,911,023 B1
DATED : June 28, 2005
INVENTOR(S) : Hamilton et al.

It is certified that error appears in the above-identified patent and that said Letters Patent is hereby corrected as shown below:

Column 26,
Line 20, delete "last" and insert -- least --.

Column 28,
Line 15, after "12", insert -- , --.

Column 31,
Line 4, after "configuration", insert -- wherein the fastening system has a primary direction of lead bearing and has a peel resistance in a direction other than the primary direction of load bearing greater than or equal to about 1000 grams --.

Column 33,
Line 12, delete "test" and insert -- first --.

Column 34,
Line 24, delete "hearing" and insert -- bearing --.

Signed and Sealed this

Fifteenth Day of November, 2005

JON W. DUDAS
*Director of the United States Patent and Trademark Office*